United States Patent
Polykovskiy et al.

(10) Patent No.: US 11,680,063 B2
(45) Date of Patent: Jun. 20, 2023

(54) ENTANGLED CONDITIONAL ADVERSARIAL AUTOENCODER FOR DRUG DISCOVERY

(71) Applicant: INSILICO MEDICINE IP LIMITED, Hong Kong (HK)

(72) Inventors: Daniil Polykovskiy, Moscow (RU); Artur Kadurin, Taipei (TW); Aleksandr M. Aliper, Moscow (RU); Alexander Zhebrak, Moscow (RU); Aleksandrs Zavoronkovs, Pak Shek Kok (HK)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 911 days.

(21) Appl. No.: 16/562,373

(22) Filed: Sep. 5, 2019

(65) Prior Publication Data
US 2020/0082916 A1    Mar. 12, 2020

Related U.S. Application Data

(60) Provisional application No. 62/727,926, filed on Sep. 6, 2018.

(51) Int. Cl.
*G16C 20/30* (2019.01)
*G16C 20/70* (2019.01)
(Continued)

(52) U.S. Cl.
CPC ....... *C07D 471/04* (2013.01); *G06F 18/2178* (2023.01); *G06N 3/04* (2013.01);
(Continued)

(58) Field of Classification Search
CPC ...... G06K 9/6263; G01C 20/30; G01C 20/50; G01C 20/70; G06N 3/0454; G06N 3/0472;
(Continued)

(56) References Cited

PUBLICATIONS

Chen et al., The Rise of Deep Learning in Drug Discovery, Jun. 2018, Drug Discovery Today, vol. 23, No. 6, pp. 1241-1250 (Year: 2018).*

(Continued)

*Primary Examiner* — Toan M Le
(74) *Attorney, Agent, or Firm* — Maschoff Brennan

(57) ABSTRACT

A method is provided for generating new objects having given properties, such as a specific bioactivity (e.g., binding with a specific protein). In some aspects, the method can include: (a) receiving objects (e.g., physical structures) and their properties (e.g., chemical properties, bioactivity properties, etc.) from a dataset; (b) providing the objects and their properties to a machine learning platform, wherein the machine learning platform outputs a trained model; and (c) the machine learning platform takes the trained model and a set of properties and outputs new objects with desired properties. The new objects are different from the received objects. In some aspects, the objects are molecular structures, such as potential active agents, such as small molecule drugs, biological agents, nucleic acids, proteins, antibodies, or other active agents with a desired or defined bioactivity (e.g., binding a specific protein, preferentially over other proteins).

22 Claims, 10 Drawing Sheets

(51) Int. Cl.

| | |
|---|---|
| *G16C 20/50* | (2019.01) |
| *C07D 471/04* | (2006.01) |
| *G16C 20/40* | (2019.01) |
| *G06N 3/04* | (2023.01) |
| *G06N 3/08* | (2023.01) |
| *G06F 18/21* | (2023.01) |
| *G06V 10/764* | (2022.01) |
| *G06V 10/82* | (2022.01) |

(52) U.S. Cl.
CPC ............. *G06N 3/08* (2013.01); *G06V 10/764* (2022.01); *G06V 10/82* (2022.01); *G16C 20/30* (2019.02); *G16C 20/40* (2019.02); *G16C 20/70* (2019.02)

(58) Field of Classification Search
CPC ........ G06N 3/045; G06N 3/047; G06N 3/084; G06V 10/82; G16C 20/30; G16C 20/70; G16C 20/50; G06F 18/2178; G06F 18/2413
See application file for complete search history.

(56) References Cited

PUBLICATIONS

Angermueller, C.; Parnamaa, T.; Parts, L.; Stegle, O. Deep learning for computational biology. Mol. Syst. Biol. 2016, 12, 878.
Mamoshina, P.; Vieira, A.; Putin, E.; Zhavoronkov, A. Applications of Deep Learning in Biomedicine. Molecular Pharmaceutics 2016, 13, 1445-1454.
Miotto, R.; Wang, F.; Wang, S.; Jiang, X.; Dudley, J. T. Deep learning for healthcare: review, opportunities and challenges. Briefings in Bioinformatics 2017.
Chen, H.; Engkvist, O.; Wang, Y.; Olivecrona, M.; Blaschke, T. The rise of deep learning in drug discovery. Drug Discovery Today 2018.
Ching, T et al. Opportunities and obstacles for deep learning in biology and medicine. J R Soc Interface 2018, 15.
Putin, E.; Mamoshina, P.; Aliper, A.; Korzinkin, M.; Moskalev, A.; Kolosov, A.; Ostrovskiy, A.; Cantor, C.; Vijg, J. Zhavoronkov, A. Deep biomarkers of human aging: Application of deep neural networks to biomarker development. Aging (Albany NY) 2016, 8, 1021-1033.
Vanhaelen, Q.; Mamoshina, P.; Aliper, A. M.; Artemov, A.; Lezhnina, K.; Ozerov, I.; Labat, I.; Zhavoronkov, A. Design of efficient computational workflows for in silico drug repurposing. Drug Discovery Today 2017, 22, 210-222.
Ozerov, I. V. et al. In silico Pathway Activation Network Decomposition Analysis (iPANDA) as a method for biomarker development. Nature Communications 2016, 7, 13427.
Wallach, I.; Dzamba, M.; Heifets, A. AtomNet: A Deep Convolutional Neural Network for Bioactivity Prediction in Structure-based Drug Discovery. CoRR 2015, abs/1510.02855.
Gomes, J.; Ramsundar, B.; Feinberg, E. N.; Pande, V. S. Atomic Convolutional Networks for Predicting Protein-Ligand Binding Affinity. CoRR 2017, abs/1703.10603.
Ragoza, M.; Hochuli, J.; Idrobo, E.; Sunseri, J.; Koes, D. R. Protein-Ligand Scoring with Convolutional Neural Networks. Journal of Chemical Information and Modeling 2017, 57, 942-957.
Kingma, D. P.; Welling, M. Auto-encoding variational bayes. arXiv 2013, abs/1312.6114.
Duvenaud, D. K.; Maclaurin, D.; Aguilera-lparraguirre, J.; Gómez-Bombarelli, R.; Hirzel, T.; Aspuru-Guzik, A.; Adams, R. P. Convolutional Networks on Graphs for Learning Molecular Fingerprints. 2015.
Kearnes, S. M.; McCloskey, K.; Berndl, M.; Pande, V. S.; Riley, P. Molecular graph convolutions: moving beyond fingerprints. Journal of computer-aided molecular design 2016, 30 8, 595-608.
Gilmer, J.; Schoenholz, S. S.; Riley, P. F.; Vinyals, O.; Dahl, G. E. Neural Message Passing for Quantum Chemistry. 2017.
Gómez-Bombarelli, R.; Wei, J. N.; Duvenaud, D.; Hernández-Lobato, J. M.; Sánchez-Lengeling, B.; Sheberla, D. Aguilera-Iparraguirre, J.; Hirzel, T. D.; Adams, R. P.; Aspuru-Guzik, A. Automatic chemical design using a data-driven continuous representation of molecules. ACS Central Science 2018.
Goodfellow, I.; Pouget-Abadie, J.; Mirza, M.; Xu, B.; Warde-Farley, D.; Ozair, S.; Courville, A.; Bengio, Y. Generative adversarial nets. 2014, 2672-2680.
Makhzani, A.; Shlens, J.; Jaitly, N.; Goodfellow, I. Adversarial Autoencoders. 2016.
Radford, A.; Metz, L.; Chintala, S. Unsupervised representation learning with deep convolutional generative adversarial networks. International Conference on Learning Representations 2016.
Karras, T.; Aila, T.; Laine, S.; Lehtinen, J. Progressive Growing of GANs for Improved Quality, Stability, and Variation. CoRR 2017, abs/1710.10196.
Lample, G.; Zeghidour, N.; Usunier, N.; Bordes, A.; Denoyer, L.; Ranzato, M. A. Fader Networks: Manipulating Images by Sliding Attributes. 2017, 5967-5976.
Kadurin, A.; Aliper, A.; Kazennov, A.; Mamoshina, P.; Vanhaelen, Q.; Khrabrov, K.; Zhavoronkov, A. The cornucopia of meaningful leads: Applying deep adversarial au-toencoders for new molecule development in oncology. Oncotarget 2017, 8, 10883.
Jin, W.; Barzilay, R.; Jaakkola, T. Junction Tree Variational Autoencoder for Molecu-lar Graph Generation. Proceedings of the 35th International Conference on Machine Learning 2018, 80, 2323-2332.
Kuzminykh, D.; Polykovskiy, D.; Kadurin, A.; Zhebrak, A.; Baskov, I.; Nikolenko, S.; Shayakhmetov, R.; Zhavoronkov, A. 3D Molecular Representations Based on the Wave Transform for Convolutional Neural Networks. Mol. Pharm. 2018.
Sanchez-Lengeling, B.; Aspuru-Guzik, A. Inverse molecular design using machine learning: Generative models for matter engineering. Science 2018, 361, 360-365.
Sohn, K.; Lee, H.; Yan, X. Learning structured output representation using deep conditional generative models. Advances in Neural Information Processing Systems. 2015; pp. 3483-3491.
Mirza, M.; Osindero, S. Conditional Generative Adversarial Nets. CoRR 2014, abs/1411.1784.
Cheung, B.; Livezey, J. A.; Bansal, A. K.; Olshausen, B. A. Discovering Hidden Factors of Variation in Deep Networks. arXiv 2014, abs/1412.6583.
Ganin, Y.; Ustinova, E.; Ajakan, H.; Germain, P.; Larochelle, H.; Laviolette, F.; Marchand, M.; Lempitsky, V. S. Domain-Adversarial Training of Neural Networks. 2016.
Creswell, A.; Bharath, A. A.; Sengupta, B. Conditional Autoencoders with Adversarial Information Factorization. arXiv 2017, abs/1711.05175.
Michaël Mathieu, Junbo Jake Zhao, Pablo Sprechmann, Aditya Ramesh, Yann LeCun. Disentangling factors of variation in deep representation using adversarial training. In Daniel D. Lee, Masashi Sugiyama, Ulrike V. Luxburg, Isabelle Guyon, Roman Garnett, editors, Advances in Neural Information Processing Systems 29: Annual Conference on Neural Information Processing Systems 2016, Dec. 5-10, 2016, Barcelona, Spain, pp. 5041-5049, 2016. [doi].
Zhou, Z. Convolution on Graph: A High-Order and Adaptive Approach. 2017.
Segler, M. H. S.; Kogej, T.; Tyrchan, C.; Waller, M. P. Generating Focused Molecule Libraries for Drug Discovery with Recurrent Neural Networks. ACS Central Science 2017, 4, 120-131.
Gupta, A.; Müller, A. T.; Huisman, B. J. H.; Fuchs, J. A.; Schneider, P.; Schneider, G. Generative Recurrent Networks for De Novo Drug Design. Molecular Informatics 2017.
Weininger, D. SMILES, a chemical language and information system. 1. Introduction to methodology and encoding rules. 1970, 17, 1-14.
Weininger, D.; Weininger, A.; Weininger, J. L. SMILES. 2. Algorithm for generation of unique SMILES notation. Journal of chemical information and computer sciences 1989, 29, 97-101.
Blaschke, T.; Olivecrona, M.; Engkvist, O.; Bajorath, J.; Chen, H. Application of Generative Autoencoder in de Novo Molecular Design. Molecular Informatics 2017.

(56) References Cited

PUBLICATIONS

Guimaraes, G. L.; Sanchez-Lengeling, B.; Farias, P. L. C.; Aspuru-Guzik, A. Objective-Reinforced Generative Adversarial Networks (ORGAN) for Sequence Generation Models. CoRR 2017, abs/1705.10843.

Putin, E.; Asadulaev, A.; Vanhaelen, Q.; Ivanenkov, Y.; Aladinskaya, A. V.; Aliper, A.; Zhavoronkov, A. Adversarial Threshold Neural Computer for Molecular de Novo Design. Molecular Pharmaceutics 2018.

Putin, E.; Asadulaev, A.; Ivanenkov, Y.; Aladinskiy, V.; Sanchez-Lengeling, B.; Aspuru-Guzik, A.; Zhavoronkov, A. Reinforced Adversarial Neural Computer for de Novo Molecular Design. J Chem Inf Model 2018, 58, 1194-1204.

Olivecrona, M.; Blaschke, T.; Engkvist, O.; Chen, H. Molecular de-novo design through deep reinforcement learning. Journal of Cheminformatics 2017, 9.

Wieczorek, A.; Wieser, M.; Murezzan, D.; Roth, V. Learning Sparse Latent Representations with the Deep Copula Information Bottleneck. International Conference on Learning Representations 2018.

Alemi, A. A.; Fischer, I.; Dillon, J. V.; Murphy, K. Deep variational information bottleneck. International Conference on Learning Representations 2017.

Paszke, A.; Gross, S.; Chintala, S.; Chanan, G.; Yang, E.; DeVito, Z.; Lin, Z.; Desmai-son, A.; Antiga, L.; Lerer, A. Automatic differentiation in PyTorch. NIPS-W. 2017.

Williams, R. J.; Zipser, D. A Learning Algorithm for Continually Running Fully Recur-rent Neural Networks. Neural Computation 1989, 1, 270-280.

Hinton, G.; Srivastava, N.; Swersky, K. Neural Networks for Machine Learning-Lecture 6a-Overview of mini-batch gradient descent. 2012.

Belghazi, M. I.; Baratin, A.; Rajeshwar, S.; Ozair, S.; Bengio, Y.; Hjelm, D.; Courville, A. Mutual Information Neural Estimation. 2018, 80, 531-540.

Morgan, H. L. The Generation of a Unique Machine Description for Chemical Structures—A Technique Developed at Chemical Abstracts Service. Journal of Chemical Documentation 1965, 5, 107-113.

Ertl, P.; Schuffenhauer, A. Estimation of synthetic accessibility score of drug-like molecules based on molecular complexity and fragment contributions. Journal of chem-informatics 2009, 1, 8.

Landrum, G. RDKit: Open-source cheminformatics. Online). http://www.rdkit.org. Accessed 2006, 3, 2012.

Trott, O.; Olson, A. J. AutoDock Vina: improving the speed and accuracy of docking with a new scoring function, efficient optimization, and multithreading. Journal of computational chemistry 2010, 31, 455-461.

Schwartz, D. M.; Kanno, Y.; Villarino, A.; Ward, M.; Gadina, M.; O'Shea, J. J. JAK inhibition as a therapeutic strategy for immune and inflammatory diseases. Nature Reviews Drug Discovery 2017, 16, 843.

Ivanenkov, T., Balakin New Approaches to the Treatment of Inflammatory Disease. Drugs in R & D 2008, 9, 397-434.

Ivanenkov, Y.; Balakin, K.; Lavrovsky, Y. Small Molecule Inhibitors of NF-kB and JAK/STAT Signal Transduction Pathways as Promising Anti-Inflammatory Therapeu-tics. Mini reviews in medicinal chemistry 2011, 11, 55-78.

Samadi, A.; Ahmad Nasrollahi, S.; Hashemi, A.; Nassiri Kashani, M.; Firooz, A. Janus kinase (JAK) inhibitors for the treatment of skin and hair disorders: a review of literature. Journal of Dermatological Treatment 2017, 28, 476-483.

Verstovsek, S. Therapeutic potential of JAK2 inhibitors. ASH Education Program Book 2009, 2009, 636-642.

Lancman, G.; Mascarenhas, J. Should we be treating lower risk myelofibrosis patients with a JAK2 inhibitor? Expert review of hematology 2017, 10, 23-28.

Jain, T.; Mesa, R. The development, safety and efficacy of pacritinib for the treatment of myelofibrosis. Expert review of anticancer therapy 2016, 16, 1101-1108.

Gaulton, A et al. The ChEMBL database in 2017. Nucleic Acids Research 2016, 45, D945-D954.

\* cited by examiner

ENTANGLED CONDITIONAL ADVERSARIAL AUTOENCODER FOR DRUG DISCOVERY

CROSS-REFERENCE

This patent application claims priority to U.S. Provisional Application No. 62/727,926 filed Sep. 6, 2018, which provisional is incorporated herein by specific reference in its entirety.

BACKGROUND

Deep learning has been used for biomarker development, drug discovery and drug repurposing. In part, computer technology is being used in place of or to enhance standard drug discovery in order to offset the significant time and costs of identifying a potential drug and moving the potential drug through the regulatory process before it can be marketed as a commercial drug. While the standard drug discovery pipeline includes many stages, it is still a problem to find an initial set of molecules that may change the activity of a specific protein or a signaling pathway.

The hit rate of new drug candidates can be improved by removing compounds that do not show significant promise. Such compounds can be identified as unsuitable for further study at early stages with machine learning models, which can be used to estimate properties of the compound and guide the drug optimization process. Machine learning can be used to learn useful latent representations of molecules using Variational Autoencoders, graph convolutions, and graph message passing networks. Latent representation can be used to optimize chemical properties of encoded molecules using Bayesian optimization.

Recently, Generative Adversarial Networks (GAN) and Adversarial Autoencoders (AAE) have been developed for generative modeling of structured objects such as text, speech, and images. The generative models, which can be trained on molecular descriptors, 3D structure, textual notation or molecular graphs, can create novel molecular structures with desired properties such as activity against a given target-protein.

Previously, applied Supervised Adversarial Autoencoders (SAAE) have been used to generate new compounds with molecular properties as a condition. The original model achieved good results with a few simple conditions. However, generation of complex objects (e.g., molecular structures or high-resolution images) requires a large number of complex conditions with thousands of variations.

Therefore, it would be advantageous to improve a SAAE architecture and obtain significantly higher performance in the generation of novel chemical structures given complex conditions.

SUMMARY

A method for generating an object comprising: obtaining a plurality of objects and object properties thereof from a dataset; inputting the plurality of objects and object properties into a machine learning platform; creating a trained model with the machine learning platform that is trained with the plurality of objects and object properties; processing the trained model to obtain latent codes of the objects; reparameterizing the latent codes into samples of at least two marginal distributions; disentangling the latent codes for the at least two marginal distributions of latent codes; discriminating between the at least two marginal distributions with a defined property value; generating a plurality of generated objects each having the defined property value; and providing a report of the plurality of the generated objects, wherein the report defines at least one defined property value of the plurality of the generated objects. In some aspects, the method can include filtering the dataset to remove objects unlikely to have the defined property value. In some aspects, the trained model includes a supervised adversarial autoencoder. In some aspects, the trained model includes an entangled conditional adversarial autoencoder. In some aspects, the dataset includes structural data for the plurality of objects and property data for the object properties, wherein the property data includes at least one of: binding activity to a specific protein, solubility, or ease of synthesis of the objects.

In some embodiments, the method can include performing a predictive disentanglement between at least two variables with the trained model. In some aspects, the method can include: estimating dependence between two variables by computing their mutual information; and promoting independence between the two variables by minimizing their mutual information in computations. In some aspects, the method can include: optimizing loss by training a neural network q to extract information about a first variable of the two variables from the second variable and/or the latent code; and updating an encoder of the trained model to eliminate the extracted information from the latent code.

In some embodiments, the method can include performing a joint disentanglement between at least two variables with the trained model. In some aspects, the method can include: training the trained model to extract a first property from the latent code; and modifying a second property to confuse a predictor to obtain a predictive regularizer. In some aspects, the method can include: optimizing the trained model to have conditional independence of a plurality of variables for the plurality of variables; obtaining a plurality of factorized variational distributions for the plurality of variables; and optimizing a set of distributions to underestimate any remaining mutual information for the plurality of variables. In some aspects, the method can include: optimizing a factorized prior with independent labels and latent codes; sampling from a distribution of latent codes with properties of defined objects; and adversarially training the trained model to bring the sampled distribution closer to the factorized prior to provide disentanglement of the plurality of variables.

In some embodiments, the method can include performing a combined disentanglement between at least two variables with the trained model. In some aspects, the method can include: performing a predictive disentanglement to force independence between at least two marginal distributions of latent codes; and performing a joint disentanglement to reduce remaining mutual information between the at least two marginal distributions of the latent codes.

In some embodiments, the method can include: defining the property value of a generated object; generating structural analogs of a plurality of objects having the property value; processing the structural analogs through a supervised adversarial autoencoder; estimating mutual information for the structural analogs; and reducing the mutual information with a disentanglement procedure. In some aspects, the method can include: sampling lipophilicity data and synthetic accessibility from the dataset; measuring a correlation coefficient between at least one condition and at least one obtained property of the structural analogs; removing objects in the dataset from the structural analogs; and identifying at least one structural analog having the defined property value. In some aspects, the method can include: synthesizing the at last one identified structural analog; and validating the synthesized at least one structural analog to have the defined property value in vitro or in vivo. In some aspects, the method can include providing a report identifying the at least one structural analog having the defined property value and identifying the determined defined property value or a plurality of determined properties thereof.

In some embodiments, the method can include at least one of: the objects are molecules, which are represented as graphs, SMILES stings, fingerprints, InChI, or the like; the properties are biochemical properties of the objects as molecules; or the properties are physical properties of the objects as molecules.

In some embodiments, the method can include at least one of: the machine learning platform includes two or more trained machine learning models; machine learning models are neural networks such as fully connected neural networks, convolutional neural networks, or recurrent neural networks; the trained machine learning model converts the objects into the latent codes; the trained machine learning model converts the latent codes to the generated objects; the machine learning platform enforces a certain distribution of latent codes across all potential generated objects; the two or more trained machine learning models are trained with adversarial training or variational interference; a separate trained machine learning model is trained to predict object properties from the latent codes; or a separate trained machine learning model is trained to parameterize a desired distribution of latent codes of objects having the same value of properties.

In some embodiments, the method can include at least one of: an object property is binding affinity for a target protein; an object property is binding affinity for binding site on the target protein; an object property is a molecular fingerprint; or an object property is lipophilicity and/or synthetic accessibility. In some aspects, the target protein is JAK 2 and/or JAK 3; and/or a binding site is an active site forMCL1.

In some embodiments, a compound for treating a disease associated with JAK 2 can include: Compound 1; Compound 2; Compound 3; Compound 4; or Compound 5. In some aspects, the compound is Compound 5.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1A:
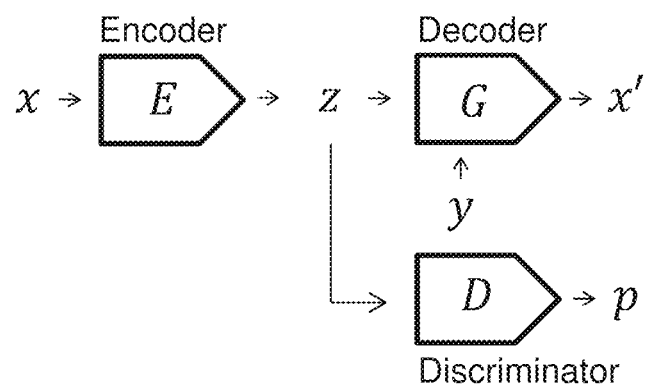
FIG. 1A shows an representation of a supervised adversarial autoencoder (SAAE) model.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Modern computational approaches and machine learning techniques accelerate the invention of new drugs. Generative models can discover novel molecular structures within hours, while conventional drug discovery pipelines require months or years of work. A new generative architecture—Entangled Conditional Adversarial Autoencoder—has been prepared that generates molecular structures based on various properties, such as activity against a specific protein, solubility, or ease of synthesis. The methods described herein can apply the proposed model to generate a novel inhibitor (e.g., Compound 5) of Janus Kinase 3, implicated in rheumatoid arthritis, psoriasis, and vitiligo. The discovered molecule was tested in vitro and showed high activity and selectivity. As such, Compound 5 can be used to treat rheumatoid arthritis, psoriasis, and vitiligo, and the symptoms thereof.

Generally, the present technology includes a method of generating a molecule, comprising: providing a model described herein; processing the model to generate a chemical structure with biological activity of a selective inhibitor of a biological process; synthesizing a molecule with the chemical structure; and validating the molecule to have the biological activity as the selective inhibitor of the biological process.

In some aspects, the protocols described herein improve SAAE architecture and demonstrate significantly higher performance in the generation of novel chemical structures given complex conditions.

Adversarial Autoencoders are generative models that model the data distribution $p_{data}(x)$ by training a regularized autoencoder. A regularizer forces a distribution of the latent code $q(z)=\int Q_E(z|x)P_{data}(x)dx$ to match a tractable prior $p(z)$. A deterministic autoencoder can include the encoding distribution $Q_E(z|x)P_{data}$ and decoding distribution $P_G(x|z)$ being parameterized by neural networks E and G respectively: $z=E(x)$ and $x=G(z)$. Regularization of the latent space is implemented by an adversarial training procedure with the Discriminator model $D(z)$. The Discriminator is trained to discriminate between samples from the latent distribution $q(z)$ and the prior $p(z)$. The Encoder E is trained to modify the latent code so the discriminator could not distinguish the latent distribution from the prior. This results in a minimax game $\min_E \max_D L_{adv}$, shown in Equation 1:

$$L_{adv} = \mathbb{E}_{x \sim P_{data}} \log D(E(x)) + \mathbb{E}_{z \sim p(z)} \log(1 - D(z)) \quad \text{(Equation 1)}$$

The adversarial training with the reconstruction penalty constitutes the following optimization task (Equation 2):

$$\min_{E,G} \max_D \mathbb{E}_{x \sim P_{data}} \log D(E(x)) + \quad \text{(Equation 2)}$$
$$\mathbb{E}_{z \sim p(z)} \log(1 - D(z)) - \mathbb{E}_{x \sim P_{data}} \log p(x | G(E(x)))$$

The framework of Adversarial Autoencoders can be extended to conditional generation. Consider data points $x \in X$ coupled with some properties $y \in Y$. Conditional generation procedure produces samples from the distribution $p(x \in y)$ for any fixed property y. Supervised AAE (SAAE) modifies the reconstruction process by concatenating the property y with the latent code z at the input of the decoder (FIG. 1A, showing a supervised adversarial autoencoder model). The training procedure becomes Equation 3:

$$\min_{E,G} \max_D \mathbb{E}_{x \sim P_{data}} \log D(E(x)) + \quad \text{(Equation 3)}$$
$$\mathbb{E}_{z \sim p(z)} \log(1 - D(z)) - \mathbb{E}_{(x,y) \sim P_{data}} \log p(x | G(E(x), y))$$

Figure 1B:
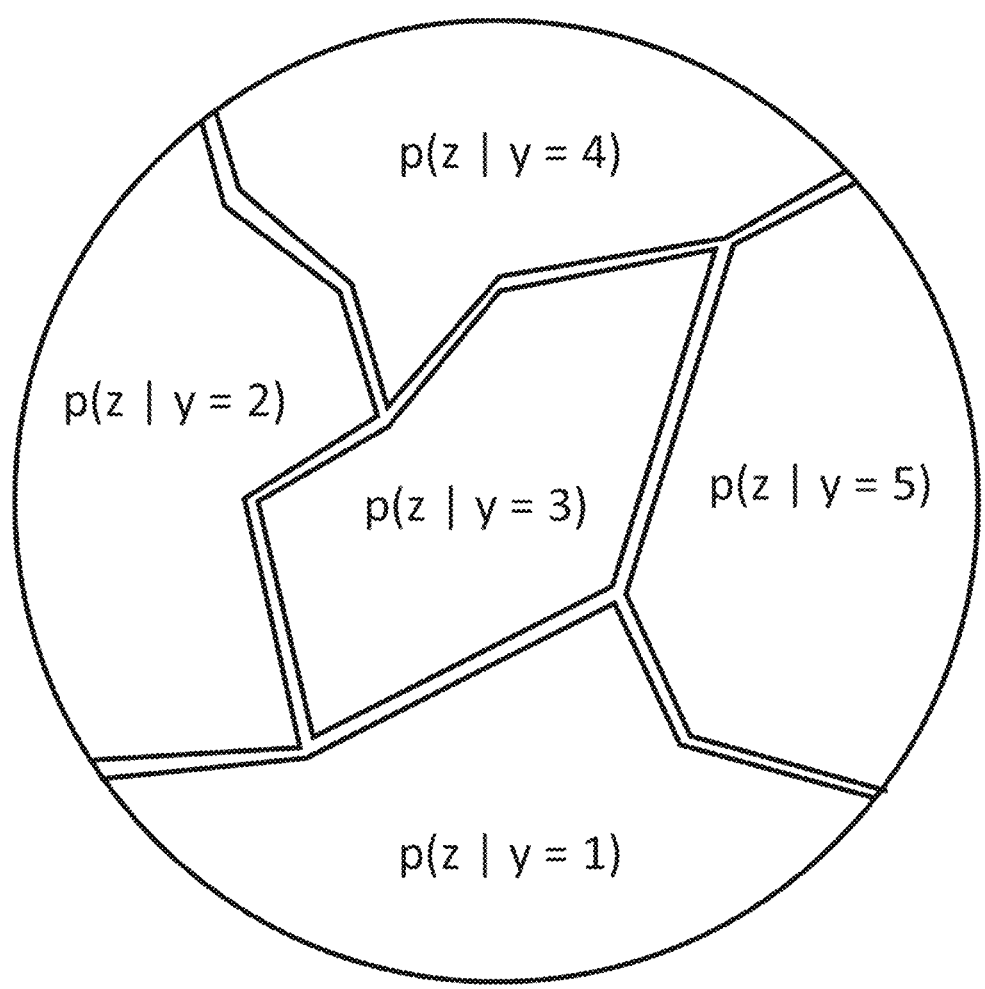
FIG. 1B shows motivation for disentanglement, whereas the marginal distribution of latent codes is p(z), but conditional distributions differ from the marginals.

It has been suggested to generate new objects by first sampling $z \sim p(z)$ and then passing the latent code through the generator $x=G(z,y)$. This process implies independence of z and y, which is not always correct. Sampling from $p(z)$ can be inconsistent, even if the model perfectly matches the latent distribution $p(z)$, and the reconstruction works well, as shown herein. Intuitively, this may happen if the marginal distribution of latent codes is $p(z)$, but for any fixed y the computations can result in a completely different distribution $p(z|y)$, as illustrated in FIG. 1B. FIG. 1B shows motivation for the disentanglement, as the marginal distribution of latent codes is $p(z)$, but conditional distributions differ from the marginals.

In this case, we cannot generate using samples from $p(z)$ for a specified y. Instead, we sample from an intractable distribution $p(z|y)$. To overcome this inconsistency issue, we introduce two methods: forcing conditional distributions $p(z|y)$ to be close to a marginal distribution $p(z)$, and learning $p(z|y)$ directly.

In some embodiments, predictive and joint approaches to disentangle latent codes z and properties y can be used in the models and protocols.

Predictive Disentanglement

In some embodiments, the protocol can estimate the dependence between two random variables by computing their mutual information (Equation 4.1):

$$I(z, y) = KL[p(z, y) | p(z)p(y)] = \int p(z, y) \log\left[\frac{p(z, y)}{p(z)p(y)}\right], \quad \text{(Equation 4.1)}$$

where KL is the Kullback-Leibler divergence.

The protocol can promote the independence between y and z by minimizing this mutual information. Since the density of the distribution $p(z,y)$ is unknown, the protocol approximates $I(z,y)$ with a variational distribution $q(y|z)$ in Equation 4:

$$I(z, y) = \quad \text{(Equation 4)}$$
$$H(y) + \mathbb{E}_{p(y,z)} \log p(y|z) + \max_q -\mathbb{E}_{p(z)} KL(p(y|z) | q(y|z)) =$$
$$H(y) + \max_q \mathbb{E}_{p(y,z)} \log q(y|z),$$

In Equation 4, H(y) is a constant entropy term, and q is a neural network trained to estimate $p(y|z)$, implying that z is obtained from data points by a deterministic mapping, the regularizer takes the following form (Equation 5):

$$R_{predictive} = \max_{q(y|E(x))} \mathbb{E}_{(x,y) \sim P_{data}} \log q(y | E(x)) \quad \text{(Equation 5)}$$

Figure 1C:
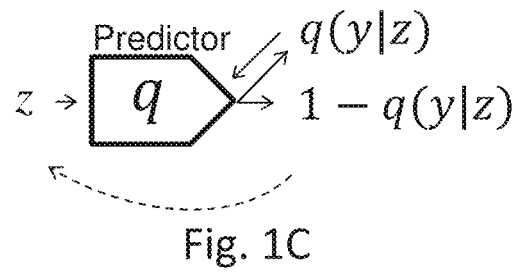
FIG. 1C shows a representation of predictive disentanglement.

The protocol can optimize this loss in an adversarial manner by first training a neural network q to extract information about y from z, and then updating the encoder to eliminate extracted features from the latent code. This method can be referred to as the Predictive disentanglement (FIG. 1C). FIG. 1C shows first training $q(y|z)$ to extract property y from the latent code (down left arrow) and then modify z to confuse the predictor (curved dashed line). The optimization procedure with a new term becomes (predictive regularizer is the last part of the Equation 6)

$$\min_{E,G} \max_{D,q} \mathbb{E}_{x \sim P_{data}} \log D(E(x)) + \mathbb{E}_{z \sim p(z)} \log(1 - D(z)) - \quad \text{(Equation 6)}$$
$$\mathbb{E}_{(x,y) \sim P_{data}} \log p(x | G(E(x), y)) + \lambda \mathbb{E}_{(x,y) \sim P_{data}} \log q(y | E(x))$$

Joint Disentanglement

In the Predictive disentanglement, the variational distribution $q(y \in E(x))$ has to be flexible enough to capture dependencies between components of y. This can be challenging: the protocol uses 166-long binary vectors as properties y, which requires a neural network to estimate a probability of $2^{166}$ possible fingerprints.

The predictive model assumes conditional independence of y components, as it allows the protocol to optimize models independently for each component. The family of factorized variational distributions can be Equation 7:

$$Q = \left\{ q(y|z) \mid q(y|z) = \prod_{i=1}^{d} q(y_i|z) \right\}$$ (Equation 7)

The protocol can underestimate the remaining mutual information by optimizing in a narrow family of distributions by Equation 8:

$$I(z, y) \geq H(y) + \max_{q \in Q} \mathbb{E}_{p(y,z)} \log q(y|z),$$ (Equation 8)

The protocol can denote the marginal distribution of a property $y_i$ as $p(y_i)$. The predictive model will only make marginal distributions independent from z, which does not imply joint independence: $q(y|z)=p(y)$. Because of this, the joint distribution can retain arbitrarily complex dependencies of y and z, and will not achieve independence.

In some embodiments, to address this issue, another disentanglement technique for the discriminator can be used. Here, the protocol can distinguish pairs (z|y) instead of discriminating samples from p(z) and p(E(x)). The protocol can optimize for the factorized prior p(z)p(y) with independent labels and latent codes. The protocol can sample from the distribution q(E(x)|y) of real latent codes along with the properties assigned to the corresponding objects. Adversarial training brings the distribution q(E(x)|y) closer to p(z)p(y) and promotes independence. This method can be referred to as the Joint disentanglement in Equation 9 (see FIG. 1D):

$$\min_{E,G} \max_{D} \mathbb{E}_{(x,y) \sim p_{data}} \log D(E(x), y) +$$ (Equation 9)

$$\mathbb{E}_{z,y \sim p(z)p(y)} \log(1 - D(z, y)) - \mathbb{E}_{(x,y) \sim p_{data}} \log p(x|G(E(x), y))$$

Figure 1D:
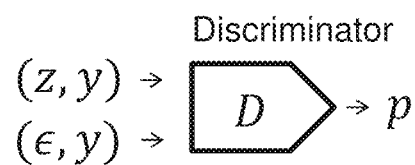
FIG. 1D shows a representation of joint disentanglement discriminates, where the protocol discriminates pairs (z, y) of latent codes and properties from pairs ($\in$; y), where $\in$~N(0,1) are independent noise samples.

FIG. 1D shows joint disentanglement discriminates, where the protocol discriminates pairs (z, y) of latent codes and properties from pairs (∈; y), where ∈~N(0,1) are independent noise samples.

Combined Disentanglement

The foregoing provides two methods of promoting independence between z and y. In the experiments, it was found that the Joint disentanglement is less stable than the Predictive disentanglement at the beginning of training. It also requires a careful hyperparameters tuning. The Predictive disentanglement, in contrast, is more stable and converges without exhaustive hyperparameter search. However, as mentioned above, the Predictive disentanglement cannot achieve complete independence of z and y in complex cases. When working together, the predictive disentanglement forces the independence of marginals $p(y_i|z)=p(y_i)$, while the joint disentanglement reduces the remaining mutual information. As a result, the protocol can be more stable with a technique that produces better results, as shown in the Experiments section. The method with both techniques the Combined disentanglement (Equation 10):

$$\min_{E,G} \max_{D,q} \mathbb{E}_{(x,y) \sim p_{data}} \log D(E(x), y) +$$ (Equation 10)

$$\mathbb{E}_{z,y \sim p(z)p(y)} \log(1 - D(z, y)) -$$

$$\mathbb{E}_{(x,y) \sim p_{data}} \log p(x|G(E(x), y)) + \lambda \mathbb{E}_{(x,y) \sim p_{data}} \log q(y|E(x))$$

Entangled Representation

The disentanglement of latent codes and labels is a powerful technique, but it imposes many constraints on the structure of a latent representation and may have a negative effect on the interpretability of latent features. For example, in ImageNet pictures, the distribution of object colors depends on a class label: cats usually have completely different colors than cars or trees. To improve the structure of the latent code, the protocol can add a dependence between y and z.

The probabilistic model becomes p(x,y,z)=p(y)p(z|y)p(x|y,z). The model can learn p(z|y) as a multivariate normal distribution with a diagonal covariance matrix parameterized by neural networks and: $p(z|y)=N(z|\mu(y),\Sigma(y))$, which is optimized during training. To ensure that parameterized posterior p(z|y) matches the embeddings of the data, the protocol trains a discriminator to distinguish samples from $q(E(x)|y)$ and $N(z|\mu(y),\Sigma(y))$. The protocol also passes the property value y to the discriminator to recognize which distribution is used as a reference for a specific object (Equation 11):

$$\min_{E,G} \max_{D,q} \mathbb{E}_{(x,y) \sim p_{data}} \log D(E(x), y) +$$ (Equation 11)

$$\mathbb{E}_{z,y \sim p(y)p(z|y)} \log(1 - D(z, y)) -$$

$$\mathbb{E}_{(x,y) \sim p_{data}} \log p(x|G(E(x), y)) + \lambda \mathbb{E}_{(x,y) \sim p_{data}} \log q(y|E(x))$$

The discrimination between two shifting distributions is an unstable procedure, as for rare values of y, the discriminator poorly estimates the density q(E(x)|y). To stabilize the training procedure, the protocol applies the reparameterization protocol, deterministically transforming latent codes into samples of the standard distribution: $\bar{z}=g_0(z,y)$ and discriminating samples from $p(\bar{z})p(y)$ and $q(g_0(E(x),y),y)$. Now, the distribution $p(\bar{z})p(y)$ does not depend on parameters and is fixed during training. For the normal distribution, the reparameterization protocol becomes $$g_\theta(z, y) = \sum_{\theta}^{\frac{1}{2}} (y)(z - \mu_\theta(y))$$

and a prior $p(\bar{z})$ is a standard normal distribution $N(0; I)$. The optimization procedure after reparameterization becomes (Equation 12):

$$\min_{E,G,\theta} \max_{D,q} \mathbb{E}_{(x,y) \sim p_{data}} \log D(g_\theta(E(x), y), y) + \qquad \text{(Equation 12)}$$

$$\mathbb{E}_{\bar{z}, y \sim p(y)p(\bar{z})} \log(1 - D(\bar{z}, y)) -$$

$$\mathbb{E}_{(x,y) \sim p_{data}} \log p(x \mid G(E(x), y))$$

Figure 1E:
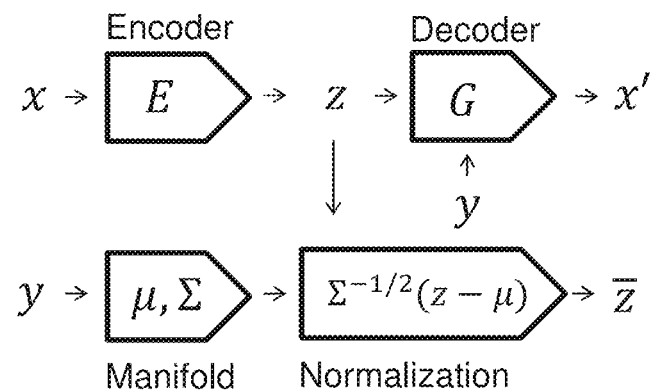
FIG. 1E shows a representation of an entangled model.

Since y and $\bar{z}$ are sampled independently, the discrimination procedure can be interpreted as a Joint disentanglement of the reparameterized latent code and its property y. This leads to the final steps to replace Joint disentanglement with the Combined disentanglement. This model is an Entangled model (FIG. 1E). The underlying optimization task is (Equation 13):

$$\min_{E,G,\theta} \max_{D,q} \mathbb{E}_{(x,y) \sim p_{data}} \log D(g_\theta(E(x), y), y) + \qquad \text{(Equation 13)}$$

$$\mathbb{E}_{\bar{z}, y \sim p(y)p(\bar{z})} \log(1 - D(\bar{z}, y)) -$$

$$\mathbb{E}_{(x,y) \sim p_{data}} \log p(x \mid G(E(x), y)) + \lambda \mathbb{E}_{(x,y) \sim p_{data}} \log q(y \mid E(x))$$

Biological Applications

In biological applications of the protocols described herein, the data may be incomplete regarding an active agent (e.g., drug, biologic agent, nucleic acid, protein, antibody, etc.). The data may include properties for only a small number of agents, but some data may be missing (e.g., values missing). To discover these missing data (e.g., missing values), expensive and time consuming in vitro or in vivo experiments may be performed. One example of this property would be the activity of a molecule against a specific protein. Other properties may require computationally expensive simulations, such as molecular dynamics or docking. Utilization of partially labeled datasets may result in an improved performance of a drug discovery pipeline. Proposed models can be naturally extended for a partially labeled data by training an imputer model h(ŷ|x) that approximates the values of unknown properties. During backpropagation, gradients for h are passed through both known and unknown positions, allowing the imputer to train jointly with the generative model. The vector with imputed properties is computed as m*y+(1−m)*ŷ, where m is a binary mask vector with zeros in positions corresponding to unknown labels.

Protocols

The protocols can use an Entangled Conditional Adversarial Autoencoder with several disentanglement techniques to improve the generation quality. The model was used for generation of molecules (e.g., Compounds 1-5) with specified property descriptors, solubility, and synthetic accessibility scores. The protocol can also be performed when the model is conditioned on target-specific properties, such as binding energy or $IC_{50}$. ECAAE can be used to discover a promising hit compound, such as Compound 5, with high selectivity against JAK3 isoform over JAK2 and RAF kinases. The proposed architecture can be used to generate novel molecules with promising scaffolds. These results suggest that ECAAE can be integrated into automated drug discovery pipelines to generate large sets of initial hypotheses for drugs in multiple disease areas.

In some embodiments, a method is provided for generating new objects having given properties. That is, the generated objects have desired properties, such as a specific bioactivity (e.g., binding with a specific protein). The objects can be generated as described herein. In some aspects, the method can include: (a) receiving objects (e.g., physical structures) and their properties (e.g., chemical properties, bioactivity properties, etc.) from a dataset; (b) providing the objects and their properties to a machine learning platform, wherein the machine learning platform outputs a trained model; and (c) the machine learning platform takes the trained model and a set of properties and outputs new objects with desired properties. The new objects are different from the received objects. In some aspects, the objects are molecular structures, such as potential active agents, such as small molecule drugs, biological agents, nucleic acids, proteins, antibodies, or other active agents with a desired or defined bioactivity (e.g., binding a specific protein, preferentially over other proteins). In some aspects, the molecular structures are represented as graphs, SMILES strings, fingerprints, InChI or other representations of the molecular structures. In some aspects, the object properties are biochemical properties of molecular structures. In some aspects, the object properties are structural properties of molecular structures.

In some embodiments of the method for generating new objects having given properties, the machine learning platform consists of two or more machine learning models. In some aspects, the two or more machine learning models are neural networks, such as fully connected neural networks, convolutional neural networks, or recurrent neural networks. In some aspects, the machine learning platform includes a trained model that converts a first object into a latent representation, and then reconstructs a second object (e.g., second object is different from the first object) back from the latent codes. In some aspects, the machine learning platform enforces a certain distribution of latent codes across all potential objects. In some aspects, the model uses adversarial training or variational inference for training. In some aspects, the model that uses a separate machine learning model to predict object properties from latent codes.

In some embodiments of the method for generating new objects having given properties, the method uses a separate machine learning model to predict object properties from latent codes. In some aspects, the model uses adversarial training or variational inference for training. In some aspects, the separate machine learning model is a neural network. In some aspects, the model uses a separate machine learning model to parameterize the desired distribution of latent codes of objects having the same value of properties, which can be a separate machine learning model that is a neural network.

In some embodiments, an object property is an activity against given target proteins. The generated object has this property of activity against one or more given target proteins. Often, the generated object specifically targets a specific target protein over other proteins (e.g., even over related proteins). In some aspects, the object property is a binding affinity towards a given site of a protein, where the generated object can have this object property. In some aspects, the object property is a molecular fingerprint, and the generated object has this object property. In some aspects, the object properties are biochemical properties of molecular structures, where the object property is a lipophilicity and/or synthetic accessibility.

In some embodiments, the object property is an activity against given target proteins, and the generated object has this property. In some aspects, the target proteins are JAK2 and JAK3. In some aspects, the object property is a binding affinity towards a given site of a protein, wherein a site of a protein is an active site of MCL1.

In some embodiments, the generated object is a molecule that is generated to have a specific activity of binding with a specific protein, such as binding to a specific binding site on that protein. The methods can include synthesizing or otherwise obtaining a physical copy of the generated object. The physical copy of the generated object can be a real molecule that can bind with a real the target protein, such as in vivo or in vitro. The molecule can then be tested in vitro and/or in vivo to validate that the molecule indeed binds to the target protein. The validation can determine the degree of binding (e.g., binding constant) for the target protein. The validation can determine the selectivity in selectively binding with the target protein over other proteins, and even over similar proteins to the target protein.

In some embodiments, a molecule is provided that is designed/generated by the protocols described herein. The molecule can have the selectively bind with the target protein.

In some embodiments, the generated molecule can be one of Compound 1, Compound 2, Compound 3, Compound 4, or Compound 5.

In some embodiments, the generated molecule is Compound 5. In some aspects, Compound 5 is validated as targeting target proteins JAK2 and JAK3. In some aspects, Compound 5 binds with MCL1. In some aspects, the target is JAK3.

Figure 3:
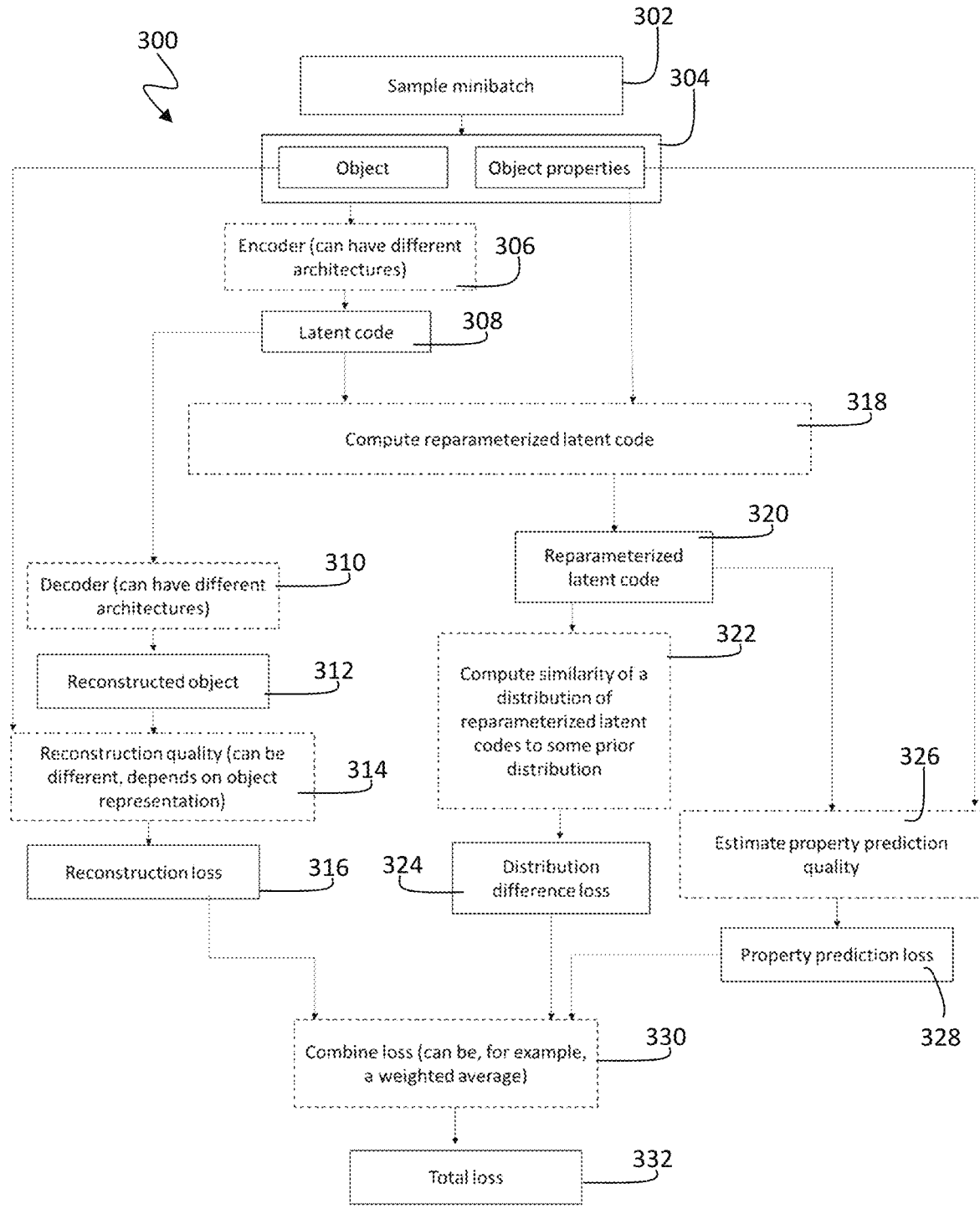
FIG. 3 illustrates a method for computing total loss during the protocol for generating an object (e.g., active agent).
Figure 3A:
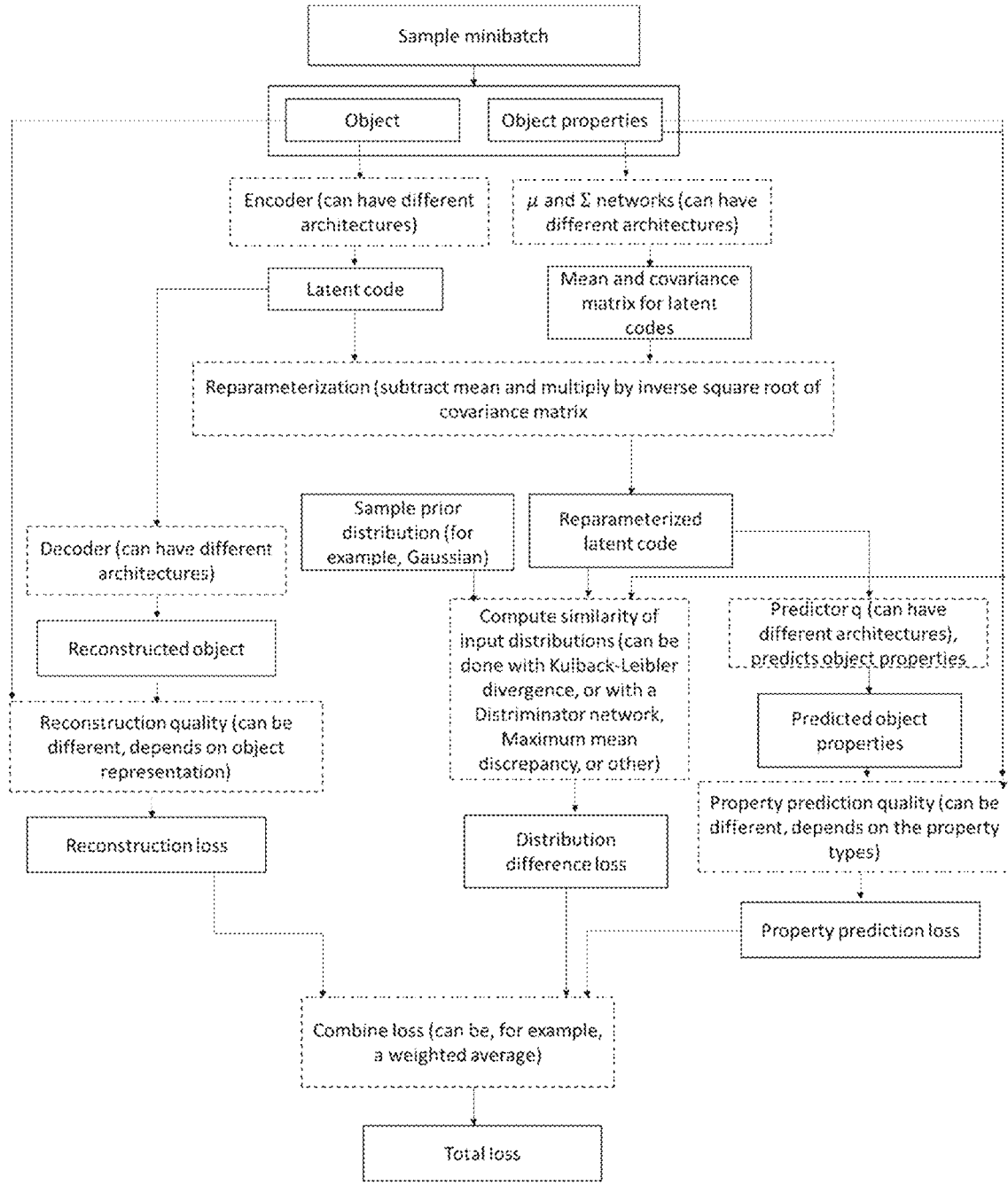
FIG. 3A shows an alternate for FIG. 3, and includes details of some computations.

FIG. 3 illustrates a method 300 for computing total loss during the protocol for generating an object (e.g., active agent). The method 300 includes: obtaining a sample minibatch (block 302); obtaining an object and the associated object properties thereof (block 304); and the data of the object and associated object properties is then processed via different paths for calculating the total loss. In one pathway, the data is processed through an encoder (block 306) to obtain a latent code (block 308). The latent code is then processed through a decoder (block 310), and a reconstructed object is obtained (block 312). The reconstructed object is for reproduction quality against the obtained object (block 314), and a reconstruction loss is obtained (block 316). In another pathway, the latent code and object properties are obtained and a reparameterized latent code is computed (block 318) to obtain the reparameterized latent code (block 320). The reparameterized latent code is then used to compute a similarity of a distribution of reparameterized latent codes to some prior distribution (block 322), and a distribution of difference loss is obtained (block 324). In another arm, the object properties are processed with the reparameterized latent code to estimate property prediction quality (block 326) and a property distribution loss is obtained (block 328). The reconstruction loss (block 316), distribution difference loss (block 324), and property prediction loss (block 328) are then processed to combine the loss (block 330) to obtain the total loss (block 332). The object(s) with the lowest total loss can be selected as a candidate object (e.g., candidate active agent, such as small molecule drug). The candidate object can then be validated to have the desired property (e.g., binding with target protein). FIG. 3A shows an alternate for FIG. 3, and includes details of some computations.

Figure 4A:
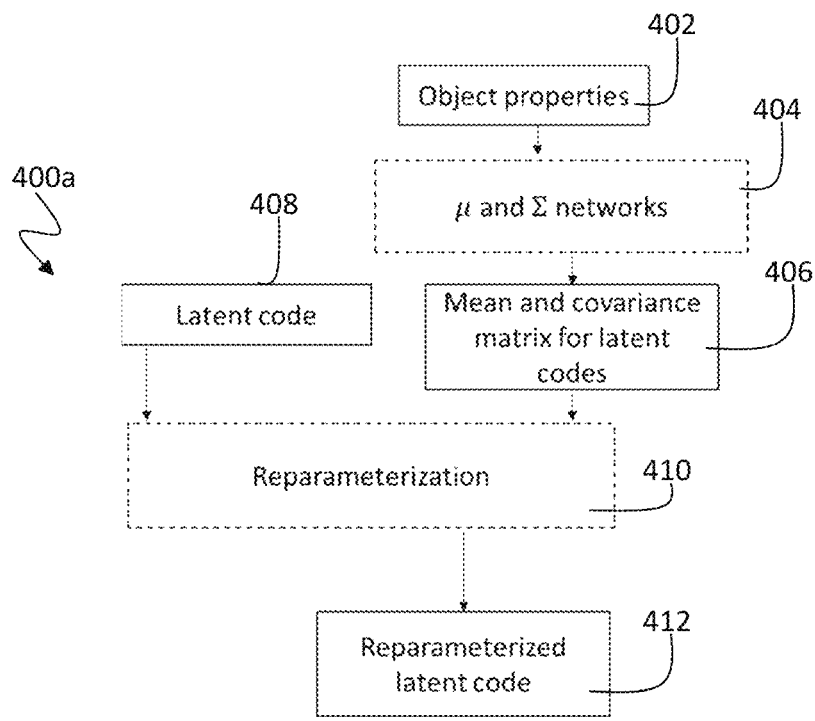
FIG. 4A illustrates a method for computing the reparameterized latent code.

FIG. 4A illustrates a method 400a for computing the reparameterized latent code. The method can include: obtaining the object properties (block 402); using the $\mu$ and $\Sigma$ networks, which can have different architectures (block 404) to obtain the mean and covariance matrix for the latent codes (block 406); obtain the latent code (block 408); and the latent code and the mean and covariance matrix for the latent codes are processed through a reparameterization (e.g., subtract mean and multiply by inverse square root of the covariance matrix) (block 410) to compute the reparameterized latent code (block 412).

Figure 4B:
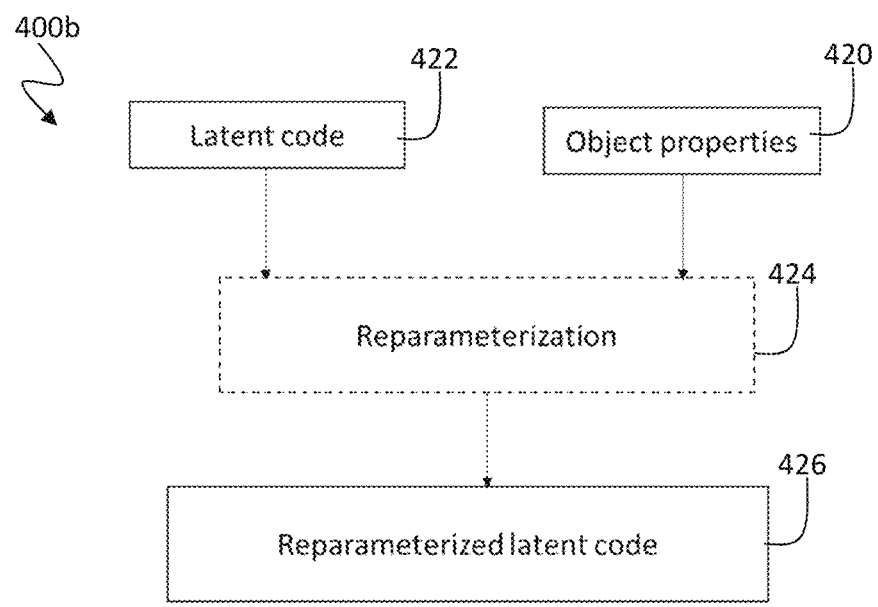
FIG. 4B illustrates another method for computing the reparameterized latent code.

FIG. 4B illustrates another method 400b for computing the reparameterized latent code. The method can include: obtaining the object properties (block 420); obtaining the latent code (block 422); processing the latent code and object properties through remarameterization (e.g., subtract mean and multiply by inverse square root of the covariance matrix) (block 424) to compute the reparameterized latent code (block 426).

Figures 4C, 4D, 4E:
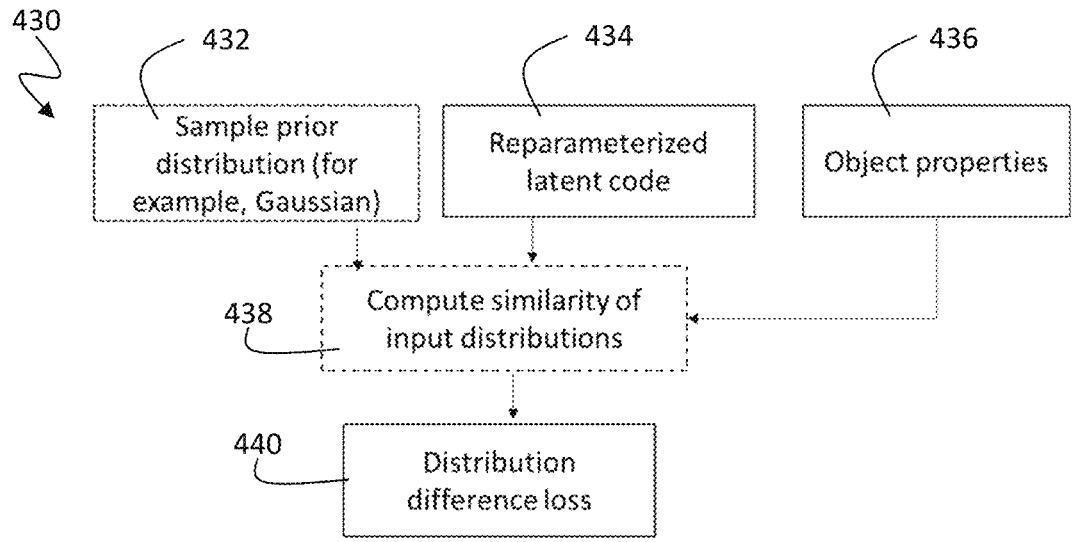
FIG. 4C illustrates a method for computing the similarity of a distribution of reparameterized latent codes to come prior distribution.
FIG. 4D illustrates a method for estimating a property prediction quality.
FIG. 4E illustrates another method for estimating a property prediction quality.

FIG. 4C illustrates a method 430 for computing the similarity of a distribution of reparameterized latent codes to come prior distribution can include: sampling a prior distribution (e.g., Gaussian distribution) (block 432); obtaining a reparameterized latent code (block 434); obtaining object properties (block 436); and computing a similarity of input distributions (block 438), which can be done with Kulback-Leibler divergence, or with a Distriminator network, Maximum mean discrepancy, or other), to obtain the distribution difference loss (block 440).

FIG. 4D illustrates a method 450 for estimating a property prediction quality, which can include: obtaining reparameterized latent code (block 452); obtaining the object properties (block 454); processing the reparameterized latent code and object properties through a predictor q (block 456) to obtain predicted object properties (block 458); determining a property prediction quality (block 460), which can be different, and depends on the property type; and obtaining the property prediction loss (block 462).

FIG. 4E illustrates another method 470 for estimating a property prediction quality, which can include: obtaining reparameterized latent code (block 472); obtaining the object properties (block 474); processing the reparameterized latent code and object properties with a constant value (e.g., for example 0 for unknown properties) (block 476); and obtaining the property prediction loss (block 478).

Figure 5:
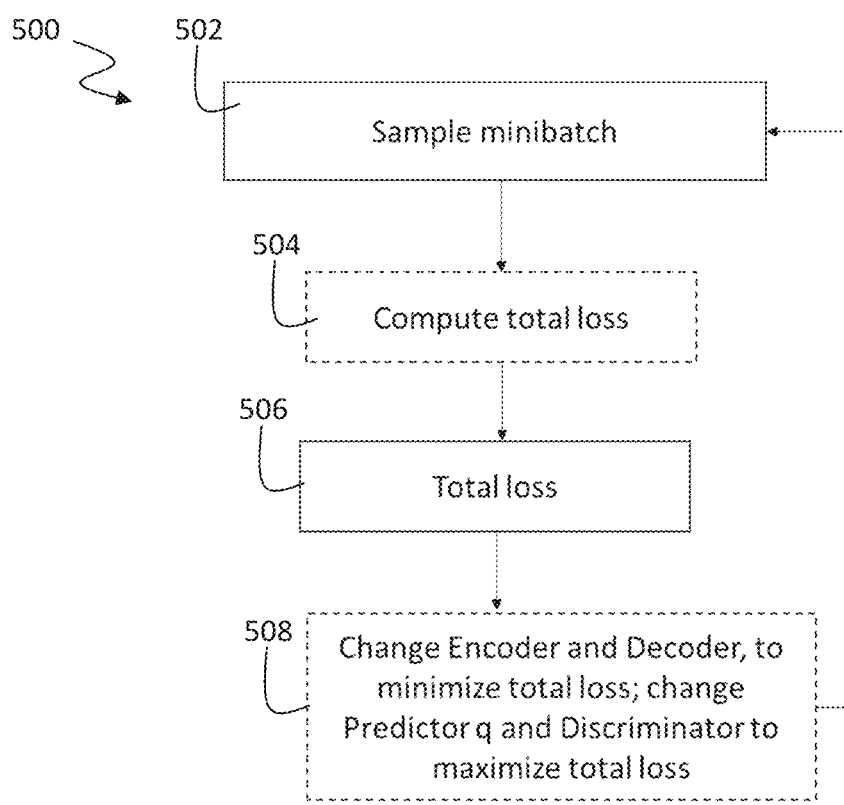
FIG. 5 illustrates a method for a training procedure.

FIG. 5 illustrates a method 500 for a training procedure, which can include: obtaining a sample minibatch (block 502); computing a total loss (block 504) to obtain the total loss (block 506), and then change the encoder and decoder to minimize the loss and/or change the predictor q and discriminator to maximize the total loss (block 508); and optionally repeating these steps until a suitable outcome is obtained. A suitable outcome can include obtaining a generated object (e.g., active agent) that has the desired properties (e.g., binds with target protein).

Figure 7A:
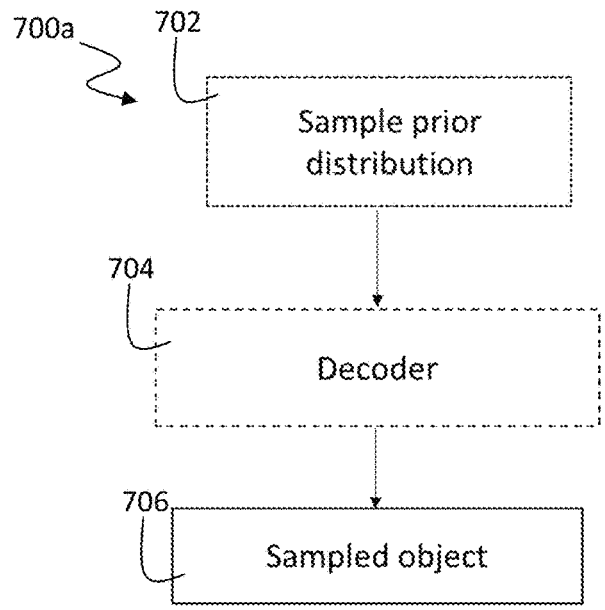
FIG. 7A illustrates a method for obtaining a new object.

FIG. 7A illustrates a method 700a for obtaining a new object, which can include: obtaining a sample prior distribution, such as a Gaussian distribution (block 702); processing the sample prior distribution through a decoder (block 704), where different decoder architectures can be used, to obtain a sampled object (block 706). The sampled object can be the generated object, and can be synthesized and validated as described herein.

Figure 7B:
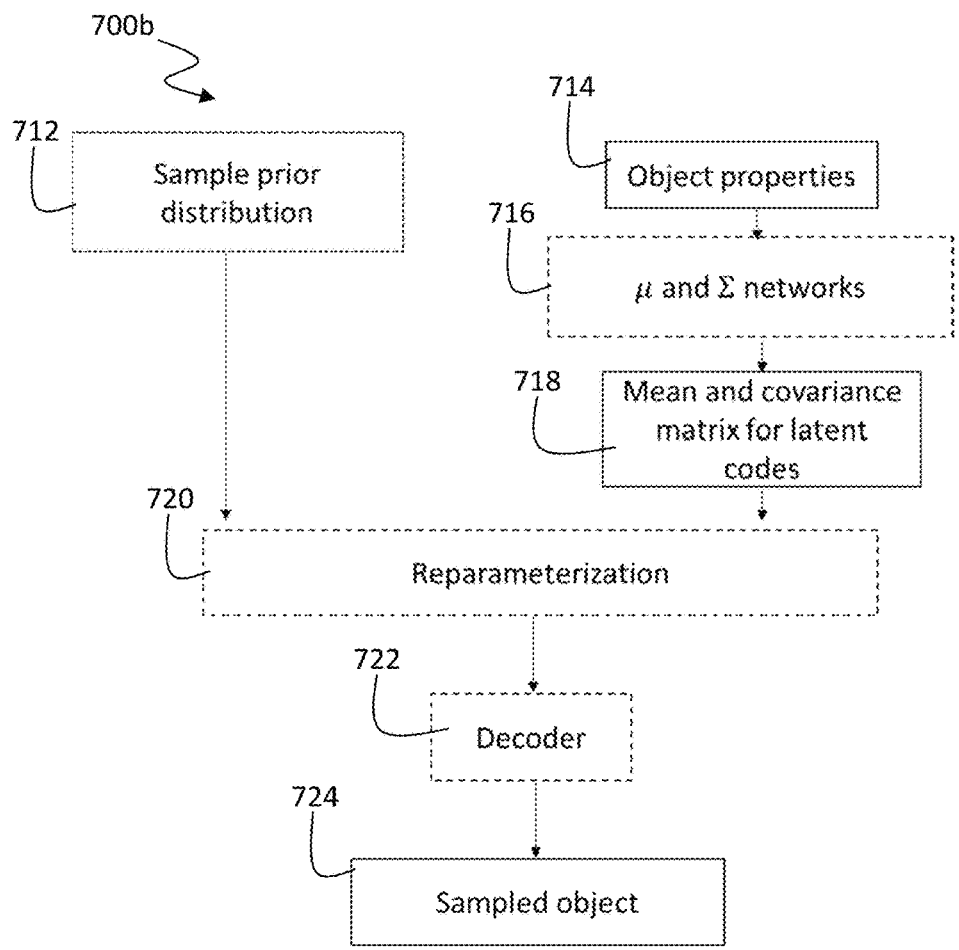
FIG. 7B illustrates another method for obtaining a new object

FIG. 7B illustrates another method 700b for obtaining a new object, which can include: obtaining a sample prior distribution, such as a Gaussian distribution (block 712); obtaining the object properties (block 714); using the $\mu$ and $\Sigma$ networks, which can have different architectures (block 716) to obtain the mean and covariance matrix for the latent codes (block 718); performing a reparameterization with the sample prior distribution and mean and covariance matrix for latent codes, which can be by multiplying by square root of covariance matrix and add mean (block 720); and then processing through a decoder, which can have different architectures (block 722), to obtain the sample object (block 724). The sampled object can be the generated object, and can be synthesized and validated as described herein.

EXPERIMENTAL

Input Data

For the experiments, the protocol used Clean Leads molecules from the ZINC database. The protocols performed an additional filtering to optimize the dataset towards the potential drug candidates and increase the hit rate of novel drug compounds. For this purpose, the protocol removed molecules that were deemed to be unlike drugs, such as charged molecules, and excluded molecules that contained atoms other than C, N, S, O, F, Cl, Br or H. The remaining set of molecules was filtered with additional drug-like filters to exclude toxic and insoluble structures. The final dataset contained roughly 1:8 million molecules encoded as strings in the form of canonical SMILES.

The protocol parsed SMILES notations to separate atoms as individual tokens. This led to a vocabulary of size 30 which contained atoms, SMILES-specific syntax elements, and special tokens, e.g., end-of-sentence. The median length of the token sequence was 36 tokens, the maximum length was 57.

Training

The model was implemented in PyTorch. The protocol used recurrent encoder and decoder with two LSTM layers of 256 units each. Hidden and cell states from the last time step of the encoder were linearly mapped onto a 64-dimensional space that the protocol used as an embedding of the input sequence. The initial state of the decoder was obtained by a linear transformation from the embedding to the hidden and cell states of the recurrent decoder. At training time, the training used the teacher forcing algorithm. At evaluation time, the protocol sampled tokens from the posterior distribution at each time step. The protocol trained models using RMSProp with an initial learning rate of 0:01, halving it after each 50;000 optimization steps. The protocol used weight decay of $10^{-5}$ for g and $10^{-6}$ for all other components. The protocol used mini-batches of size 512 and trained all models for roughly 200;000 updates, which was sufficient for the model to converge. D, q and h networks were represented by fully connected networks with two hidden layers of size 128. The network g is a fully connected network with 3 hidden layers of size 128. Based on different schedules for adversarial training, it was determined to use 4 updates of D, q and h for one update of E, G, g.

Generate Structures

In a first experiment, the protocol applied proposed models to generate structural analogs of known potent molecules. The protocol measured the similarity between compounds by comparing their fingerprints (e.g., feature vectors describing the molecular structure where each bit of the fingerprint describes the presence or absence of different molecular substructures such as acidic groups or aromatic rings). The protocol trained conditional models to generate molecules using 166-bit long Molecular ACCess System (MACCS) binary fingerprints and compared them with Supervised AAE. To produce structural analogs of existing drugs, the protocol generated 10;000 SMILES strings with each model by conditioning them on fingerprints that were excluded from the training dataset.

The protocol can report Tanimoto similarity (e.g., Jaccard index for binary vectors) and Hamming distance between fingerprints of generated molecules and molecules used as a condition. The protocol can also report the percentage of molecules that exactly matched the condition value. Results in Table 1 suggest that the entangled representation satisfies conditions more often than other models. To compare different disentanglement techniques, the protocol estimated Mutual Information (MI) between z and y using Mutual Information Neural Estimation (MINE) method. Results suggest that the Predictive disentanglement eliminates more information than the Joint disentanglement. However, as suggested above, the Predictive model cannot eliminate all mutual information, as it fits predictor in a class of fully factorized distributions. Combining both methods halved the remaining Mutual Information. Finally, adding the Predictive disentanglement to the Entangled model also reduced the Mutual Information.

TABLE 1

Performance of models trained with different disentanglement techniques using fingerprint vectors as the condition. Notice the large gap between the model with no disentanglement (corresponding to18) and other models.

| Disentanglement | Tanimoto, % | Hamming | Exact, % | Remaining MI |
| --- | --- | --- | --- | --- |
| No | 80.0 | 10.49 | 4.4 | 2.75 |
| Predictive | 86.2 | 7.13 | 11.4 | 0.64 |
| Joint | 88.7 | 5.78 | 17.4 | 1.56 |
| Combined | 91.8 | 4.18 | 27.8 | 0.32 |
| Entangled, no Predictive | 93.5 | 3.31 | 40.9 | 2.51 |
| Entangled | 93.6 | 3.28 | 41.3 | 1.30 |

Continuous Properties

The protocol also evaluated the performance of the models on continuous properties: Lipophilicity (logP) and Synthetic Accessibility (SA), obtained from RDKit. Ease of synthesis (low SA) is a desirable attribute of any prospective lead, while low logP is an important factor for a potential oral drug candidate. For trained models, the protocol jointly sampled logP and SA from the test dataset and measured Pearson correlation coefficient between specified conditions and obtained properties of generated molecules. The protocol removed generated molecules that were also present in the training dataset when computing. Results in Table 2 suggest that the Entangled model balanced the quality of both logP and SA, while other models concentrated on the simpler property—logP. Table 3 contains examples of generated molecules for extreme values of the properties. On this dataset, the difference between different disentanglement techniques in much lower than on MACCS fingerprints. This is presumably due to less interdependence between logP and SA than between 166 bits of the fingerprint, which was the limiting factor for the predictive disentanglement.

TABLE 2

Performance for continuous properties. We report
Pearson correlation r between the actual value
for generated molecules and the requested one.

| Disentanglement | logP, r | SA, r |
|---|---|---|
| No | 0.088 ± 0.005 | 0.004 ± 0.006 |
| Predictive | 0.661 ± 0.005 | 0.060 ± 0.01 |
| Joint | 0.432 ± 0.006 | 0.034 ± 0.01 |
| Combined | 0.654 ± 0.004 | 0.113 ± 0.003 |
| Entangled | 0.613 ± 0.004 | 0.431 ± 0.005 |

TABLE 3

Generated with Entangled model molecules for extreme values of logP
and SA. The upper left molecule has good logP and is easy to synthesize, while the
bottom right is less soluble and harder to obtain.

| | logP | SA | logP | SA | logP | SA | logP | SA |
|---|---|---|---|---|---|---|---|---|
| Requested | 0.00 | 1.00 | 4.00 | 1.00 | 0.00 | 5.00 | 4.00 | 5.00 |
| Actual | 0:30 | 1.77 | 4.34 | 1.66 | 0.12 | 5.03 | 4.25 | 4.58 |
| Molecule | Compound 1 | | Compound 2 | | Compound 3 | | Compound 4 | |

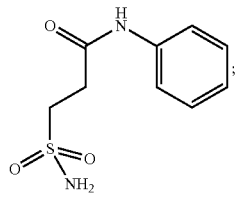

Compound 1

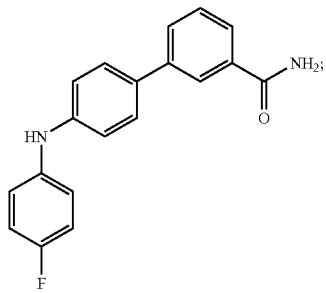

Compound 2

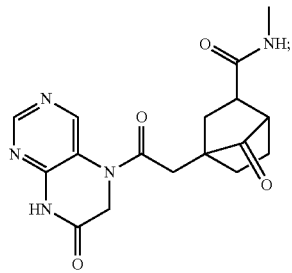

Compound 3

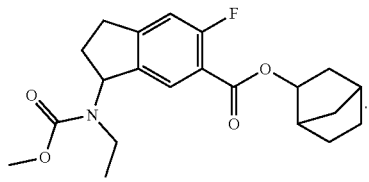

Compound 4

Semi-Supervised Data

To evaluate the semi-supervised models, the protocol computed the binding energy of 140000 molecules from the AID1022 bioassay to the leukemia-related protein MCL1 with AutoDock Vina. The binding energy E is an important value that shows how well a molecule can fit in an active site of a protein. Large negative value of E corresponds to the high binding affinity. The protocol also added logP and SA values described in the previous section to the properties. Generation results are reported in the Table 4. In the semi-supervised scenario, the entangled model often satisfies all three conditions, while other models seem to ignore SA and binding energy. The protocol also evaluated the coefficient of determination R2 of the imputation quality $h(\hat{y}|x)$ and observed it to be similar for all models with value of 0.99 for logP, 0.95 for SA, and 0.6 for E.

TABLE 4

Performance of semi-supervised models on partially labeled binding energy dataset in terms of Pearson correlation r between the requested value and the generated one.

| Disentanglement | logP, r | SA, r | E, r |
| --- | --- | --- | --- |
| No | 0.311 ± 0.01 | 0.0522 ± 0.009 | 0.02 ± 0.04 |
| Predictive | 0.687 ± 0.006 | 0.0893 ± 0.008 | 0.063 ± 0.05 |
| Joint | 0.595 ± 0.007 | 0.0838 ± 0.008 | 0109 ± 0.04 |
| Combined | 0.677 ± 0.007 | 0.0896 ± 0.007 | 0.116 ± 0.04 |
| Entangled | 0.804 ± 0.005 | 0.593 ± 0.007 | 0.406 ± 0.04 |

Results suggest that the auxiliary task of predicting values of the condition helps improving conditional generation by stabilizing encoder training for most of the models.

In this experiment, the entangled model was able to satisfy conditions significantly better than the others. Comparing different disentanglement techniques, Combined model compromised the performance on logP for the better statistics on E. The data shows that the Joint disentanglement was not able to capture correlation between different properties components. Finally, the protocol generated a few molecules conditioned on properties of the molecule (Compound 5) with the lowest binding energy in the dataset: E=11.1, logP=3.95, SA=1.8. Interestingly, two of the generated molecules (Compounds 1 and 2) had a binding energy of E=11.7, demonstrating higher binding affinity towards the target.

Validation

In this section, the protocol can include applying the model to the drug discovery pipeline by generating a selective inhibitor of a JAK3 kinase. The Janus Kinase (JAK) family contains four members—JAK1-3 and TYK2, with a different therapeutic significance. Janus Kinase 3 (JAK3) is a promising biological target against rheumatoid arthritis, psoriasis, alopecia and vitiligo. Currently, there are more than 10 novel small-molecule JAK inhibitors with an improved selectivity in different stages of clinical trials, therefore, the protocol can focus on selective JAK3 kinase inhibitors.

Figure 2A:
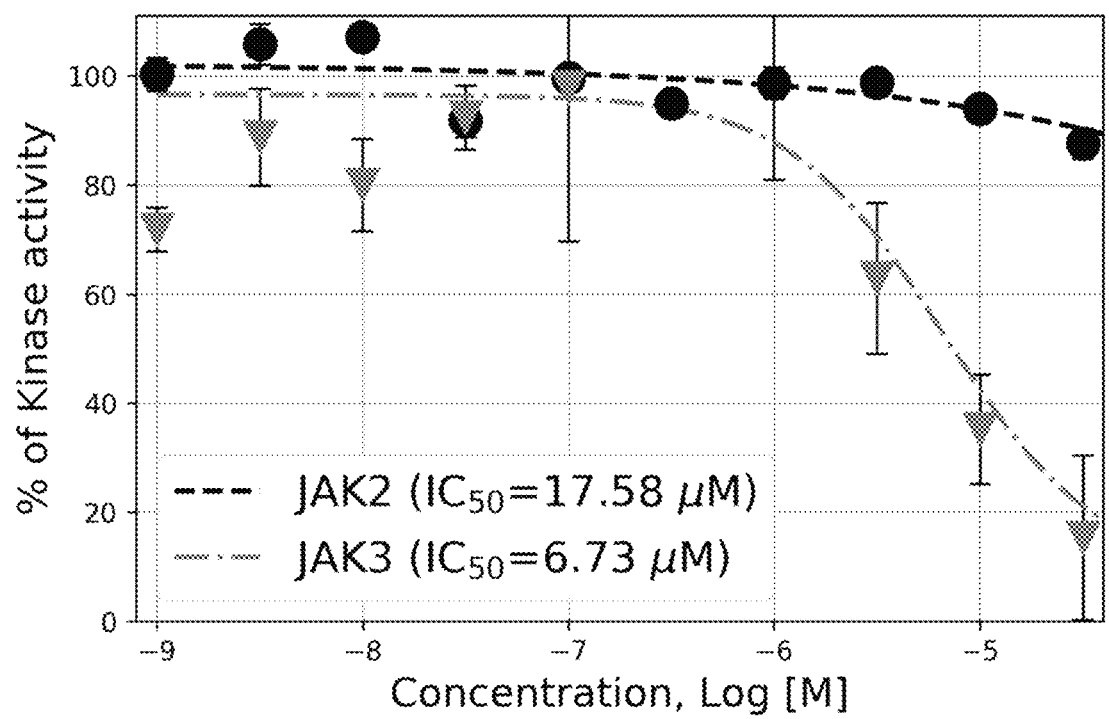
FIG. 2A shows the effectiveness of the discovered molecule Compound 5 in inhibiting the JAK2 and JAK3 kinases.
Figure 2B:
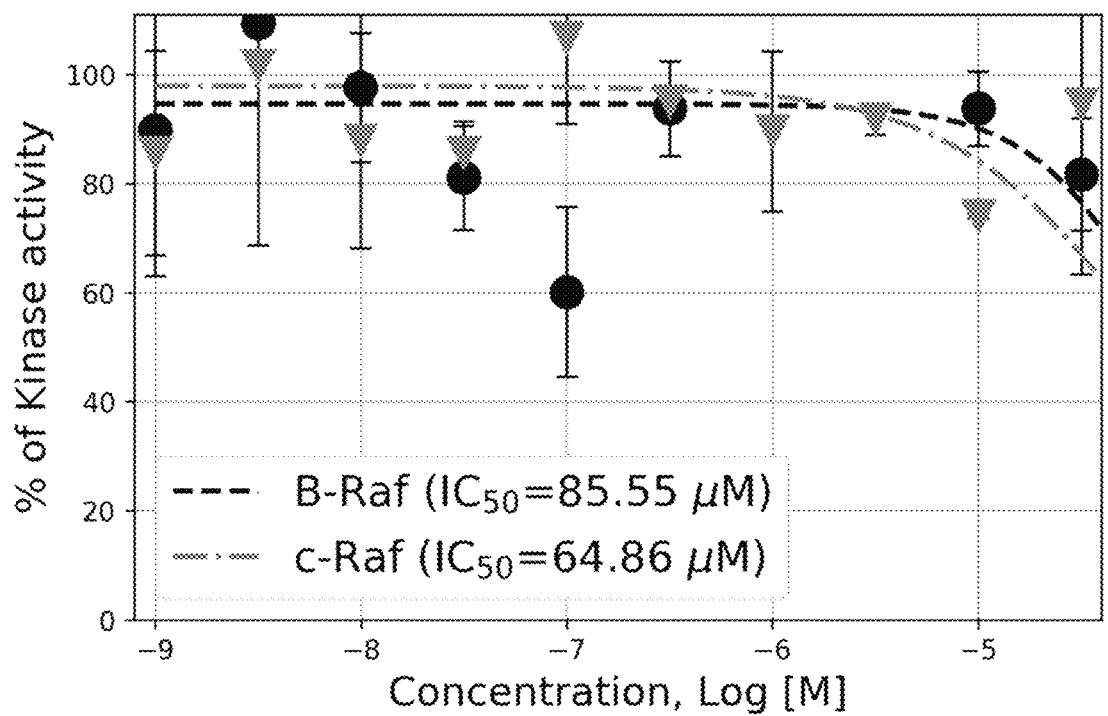
FIG. 2B shows the specificity of Compound 5 for JAK3.

To discover a selective compound, the protocol collected a database of known inhibitors of JAK2 and JAK3 from the ChEMBL database and trained a semi-supervised Entangled AAE model conditioned on the activity of molecules for JAK2 and JAK3. The protocol specified high activity against JAK3 and low activity against JAK2 as a condition. Using the trained model, the protocol was specified for high activity against JAK3 and low activity against JAK2 as the condition. The protocol generated 300;000 molecules and passed them through a series of filters, including molecular docking, prediction of side effects, and chemical properties. This reduced the number of molecules to roughly 5000. Selected molecules were used for simulation of molecular dynamics, which resulted in a set of 100 most promising molecules. Out of these molecules, medicinal chemists selected the most promising molecule, according to their experience. The chosen molecule was synthesized and tested in vitro against JAK2 and JAK3 as well as two other kinases—B-Raf and c-Raf. The activity was measured in terms of $IC_{50}$, a concentration at which the protein works at the half of its maximal activity. A molecule is considered an initial hit if its $IC_{50}$ against a target protein is less than 10 M. The discovered molecule, Compound 5, was shown to be active for JAK3 ($IC_{50}$=6.73 M) and inactive for JAK2 ($IC_{50}$=17.58 mM), B-Raf ($IC_{50}$=85.55 M) and c-Raf ($IC_{50}$=64.86 M). Dose-response curves are shown in FIGS. 2A and 2B. FIG. 2A shows the effectiveness of the discovered molecule Compound 5 in inhibiting the JAK2 and JAK3 kinases. $IC_{50}$ for JAK3 shows micromolar activity. Discovered molecule Compound 5 is active for JAK3, but not JAK2. Right: Inhibition of B-Raf and c-Raf. The discovered molecule Compound 5 does not inhibit these proteins, which suggests its high specificity.

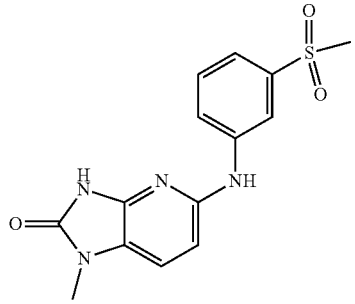

Compound 5

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems as well as network elements, base stations, femtocells, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 6:
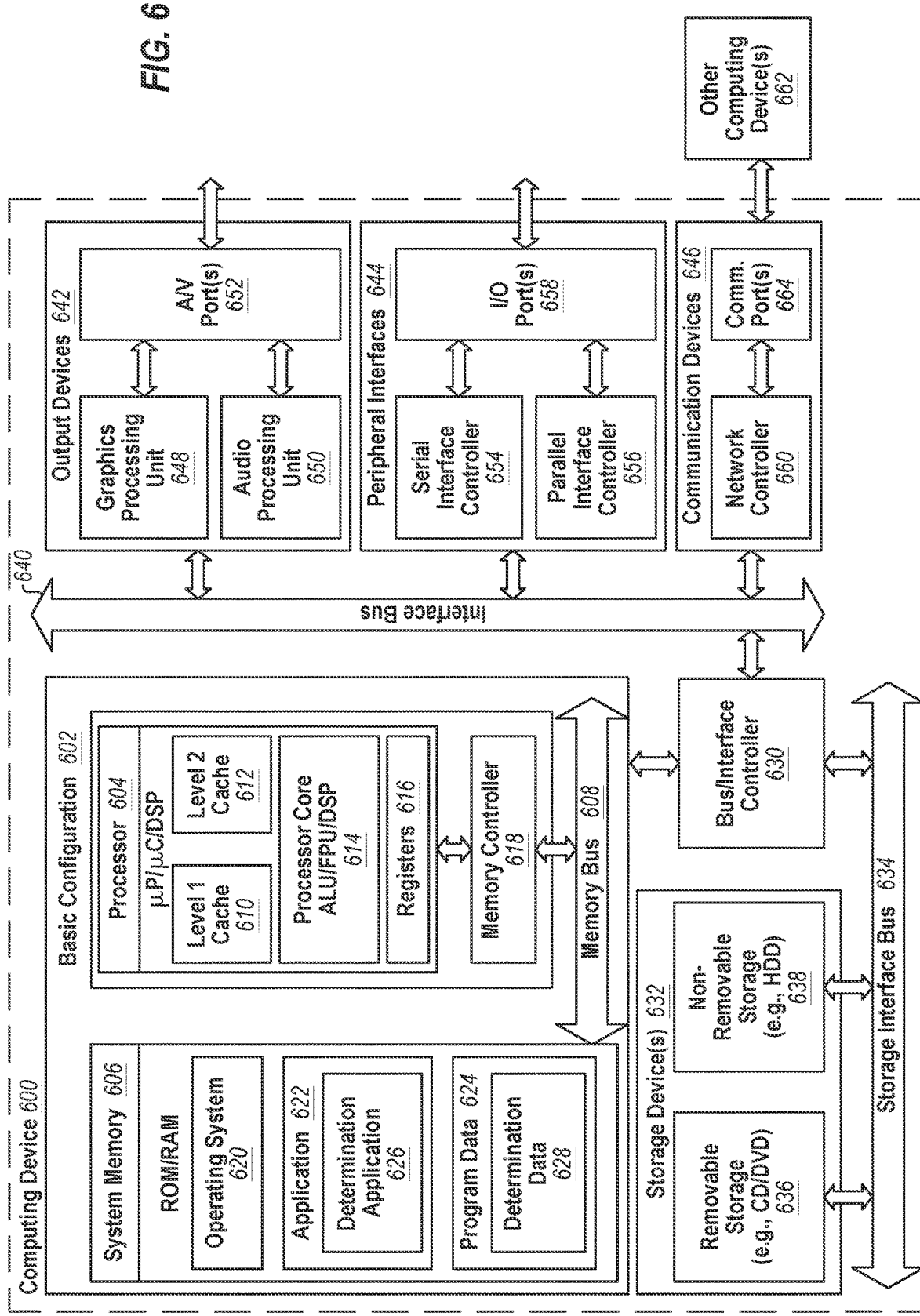
FIG. 6 includes a schematic representation of a computing system that can perform the computational methods (e.g., steps to computationally generate object).

FIG. 6 shows an example computing device 600 that is arranged to perform any of the computing methods described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (µP), a microcontroller (µC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

This patent cross-references: U.S. application Ser. No. 16/015,990 filed Jun. 2, 2018; U.S. application Ser. No. 16/134,624 filed Sep. 18, 2018; U.S. application Ser. No. 62/727,926 filed Sep. 6, 2018; U.S. application Ser. No. 62/746,771 filed Oct. 17, 2018; and U.S. Application Ser. No. 62/809,413 filed Feb. 22, 2019; which applications are incorporated herein by specific reference in their entirety.

All references recited herein are incorporated herein by specific reference in their entirety.

REFERENCES (1) Angermueller, C.; Parnamaa, T.; Parts, L.; Stegle, O. Deep learning for computational biology. Mol. Syst. Biol. 2016, 12, 878.

(2) Mamoshina, P.; Vieira, A.; Putin, E.; Zhavoronkov, A. Applications of Deep Learning in Biomedicine. Molecular Pharmaceutics 2016, 13, 1445-1454.

(3) Miotto, R.; Wang, F.; Wang, S.; Jiang, X.; Dudley, J. T. Deep learning for healthcare: review, opportunities and challenges. Briefings in Bioinformatics 2017, (4) Chen, H.; Engkvist, O.; Wang, Y.; Olivecrona, M.; Blaschke, T. The rise of deep learning in drug discovery. Drug Discovery Today 2018, (5) Ching, T. et al. Opportunities and obstacles for deep learning in biology and medicine. J R Soc Interface 2018, 15.

(6) Putin, E.; Mamoshina, P.; Aliper, A.; Korzinkin, M.; Moskalev, A.; Kolosov, A.; Ostrovskiy, A.; Cantor, C.; Vijg, J.; Zhavoronkov, A. Deep biomarkers of human aging: Application of deep neural networks to biomarker development. Aging (Albany N.Y.) 2016, 8, 1021-1033.

(7) Vanhaelen, Q.; Mamoshina, P.; Aliper, A. M.; Artemov, A.; Lezhnina, K.; Ozerov, I.; Labat, I.; Zhavoronkov, A. Design of efficient computational workflows for in silico drug repurposing. Drug Discovery Today 2017, 22, 210-222.

(8) Ozerov, I. V. et al. In silico Pathway Activation Network Decomposition Analysis (iPANDA) as a method for biomarker development. Nature Communications 2016, 7, 13427.

(9) Wallach, I.; Dzamba, M.; Heifets, A. AtomNet: A Deep Convolutional Neural Network for Bioactivity Prediction in Structure-based Drug Discovery. CoRR 2015, abs/1510.02855.
(10) Gomes, J.; Ramsundar, B.; Feinberg, E. N.; Pande, V. S. Atomic Convolutional Networks for Predicting Protein-Ligand Binding Affinity. CoRR 2017, abs/1703.10603.
(11) Ragoza, M.; Hochuli, J.; Idrobo, E.; Sunseri, J.; Koes, D. R. Protein—Ligand Scoring with Convolutional Neural Networks. Journal of Chemical Information and Modeling 2017, 57, 942-957.
(12) Kingma, D. P.; Welling, M. Auto-encoding variational bayes. arXiv 2013, abs/1312.6114.
(13) Duvenaud, D. K.; Maclaurin, D.; Aguilera-Iparraguirre, J.; Gómez-Bombarelli, R.; Hirzel, T.; Aspuru-Guzik, A.; Adams, R. P. Convolutional Networks on Graphs for Learning Molecular Fingerprints. 2015,
(14) Kearnes, S. M.; McCloskey, K.; Berndl, M.; Pande, V. S.; Riley, P. Molecular graph convolutions: moving beyond fingerprints. Journal of computer-aided molecular design 2016, 30 8, 595-608.
(15) Gilmer, J.; Schoenholz, S. S.; Riley, P. F.; Vinyals, O.; Dahl, G. E. Neural Message Passing for Quantum Chemistry. 2017,
(16) Gómez-Bombarelli, R.; Wei, J. N.; Duvenaud, D.; Hernandez-Lobato, J. M.; Sánchez-Lengeling, B.; Sheberla, D.; Aguilera-Iparraguirre, J.; Hirzel, T. D.; Adams, R. P.; Aspuru-Guzik, A. Automatic chemical design using a data-driven continuous representation of molecules. ACS Central Science 2018,
(17) Goodfellow, I.; Pouget-Abadie, J.; Mirza, M.; Xu, B.; Warde-Farley, D.; Ozair, S.; Courville, A.; Bengio, Y. Generative adversarial nets. 2014, 2672-2680.
(18) Makhzani, A.; Shlens, J.; Jaitly, N.; Goodfellow, I. Adversarial Autoencoders. 2016,
(19) Radford, A.; Metz, L.; Chintala, S. Unsupervised representation learning with deep convolutional generative adversarial networks. International Conference on Learning Representations 2016,
(20) Karras, T.; Aila, T.; Laine, S.; Lehtinen, J. Progressive Growing of GANs for Improved Quality, Stability, and Variation. CoRR 2017, abs/1710.10196.
(21) Lample, G.; Zeghidour, N.; Usunier, N.; Bordes, A.; DENOYER, L.; Ranzato, M. A. Fader Networks: Manipulating Images by Sliding Attributes. 2017, 5967-5976.
(22) Kadurin, A.; Aliper, A.; Kazennov, A.; Mamoshina, P.; Vanhaelen, Q.; Khrabrov, K.; Zhavoronkov, A. The cornucopia of meaningful leads: Applying deep adversarial autoencoders for new molecule development in oncology. Oncotarget 2017, 8, 10883.
(23) Jin, W.; Barzilay, R.; Jaakkola, T. Junction Tree Variational Autoencoder for Molecular Graph Generation. Proceedings of the 35th International Conference on Machine Learning 2018, 80, 2323-2332.
(24) Kuzminykh, D.; Polykovskiy, D.; Kadurin, A.; Zhebrak, A.; Baskov, I.; Nikolenko, S.; Shayakhmetov, R.; Zhavoronkov, A. 3D Molecular Representations Based on the Wave Transform for Convolutional Neural Networks. Mol. Pharm. 2018,
(25) Sanchez-Lengeling, B.; Aspuru-Guzik, A. Inverse molecular design using machine learning: Generative models for matter engineering. Science 2018, 361, 360-365.
(26) Sohn, K.; Lee, H.; Yan, X. Learning structured output representation using deep conditional generative models. Advances in Neural Information Processing Systems. 2015; pp 3483-3491.
(27) Mirza, M.; Osindero, S. Conditional Generative Adversarial Nets. CoRR 2014, abs/1411.1784.
(28) Cheung, B.; Livezey, J. A.; Bansal, A. K.; Olshausen, B. A. Discovering Hidden Factors of Variation in Deep Networks. arXiv 2014, abs/1412.6583.
(29) Ganin, Y.; Ustinova, E.; Ajakan, H.; Germain, P.; Larochelle, H.; Laviolette, F.; Marchand, M.; Lempitsky, V. S. Domain-Adversarial Training of Neural Networks. 2016,
(30) Creswell, A.; Bharath, A. A.; Sengupta, B. Conditional Autoencoders with Adversarial Information Factorization. arXiv 2017, abs/1711.05175.
(31) Mathieu, M. F.; Zhao, J. J.; Zhao, J.; Ramesh, A.; Sprechmann, P.; LeCun, Y. In Advances in Neural Information Processing Systems 29 ; Lee, D. D., Sugiyama, M., Luxburg, U. V., Guyon, I., Garnett, R., Eds.; Curran Associates, Inc., 2016; pp 5040-5048.
(32) Zhou, Z. Convolution on Graph: A High-Order and Adaptive Approach. 2017,
(33) Segler, M. H. S.; Kogej, T.; Tyrchan, C.; Waller, M. P. Generating Focused Molecule Libraries for Drug Discovery with Recurrent Neural Networks. ACS Central Science 2017, 4, 120-131.
(34) Gupta, A.; Willer, A. T.; Huisman, B. J. H.; Fuchs, J. A.; Schneider, P.; Schneider, G. Generative Recurrent Networks for De Novo Drug Design. Molecular Informatics 2017,
(35) Weininger, D. SMILES, a chemical language and information system. 1. Introduction to methodology and encoding rules. 1970, 17, 1-14.
(36) Weininger, D.; Weininger, A.; Weininger, J. L. SMILES. 2. Algorithm for generation of unique SMILES notation. Journal of chemical information and computer sciences 1989, 29, 97-101.
(37) Blaschke, T.; Olivecrona, M.; Engkvist, O.; Bajorath, J.; Chen, H. Application of Generative Autoencoder in de Novo Molecular Design. Molecular Informatics 2017,
(38) Guimaraes, G. L.; Sanchez-Lengeling, B.; Farias, P. L. C.; Aspuru-Guzik, A. Objective-Reinforced Generative Adversarial Networks (ORGAN) for Sequence Generation Models. CoRR 2017, abs/1705.10843.
(39) Putin, E.; Asadulaev, A.; Vanhaelen, Q.; Ivanenkov, Y.; Aladinskaya, A. V.; Aliper, A.; Zhavoronkov, A. Adversarial Threshold Neural Computer for Molecular de Novo Design. Molecular Pharmaceutics 2018,
(40) Putin, E.; Asadulaev, A.; Ivanenkov, Y.; Aladinskiy, V.; Sanchez-Lengeling, B.; Aspuru-Guzik, A.; Zhavoronkov, A. Reinforced Adversarial Neural Computer for de Novo Molecular Design. J Chem Inf Model 2018, 58, 1194-1204.
(41) Olivecrona, M.; Blaschke, T.; Engkvist, O.; Chen, H. Molecular de-novo design through deep reinforcement learning. Journal of Cheminformatics 2017, 9.
(42) Wieczorek, A.; Wieser, M.; Murezzan, D.; Roth, V. Learning Sparse Latent Representations with the Deep Copula Information Bottleneck. International Conference on Learning Representations 2018,
(43) Alemi, A. A.; Fischer, I.; Dillon, J. V.; Murphy, K. Deep variational information bottleneck. International Conference on Learning Representations 2017,
(44) Paszke, A.; Gross, S.; Chintala, S.; Chanan, G.; Yang, E.; DeVito, Z.; Lin, Z.; Desmaison, A.; Antiga, L.; Lerer, A. Automatic differentiation in PyTorch. NIPS-W. 2017.
(45) Williams, R. J.; Zipser, D. A Learning Algorithm for Continually Running Fully Recurrent Neural Networks. Neural Computation 1989, 1, 270-280.
(46) Hinton, G.; Srivastava, N.; Swersky, K. Neural Networks for Machine Learning-Lecture 6a-Overview of mini-batch gradient descent. 2012.

(47) Belghazi, M. I.; Baratin, A.; Rajeshwar, S.; Ozair, S.; Bengio, Y.; Hjelm, D.; Courville, A. Mutual Information Neural Estimation. 2018, 80, 531-540.
(48) Morgan, H. L. The Generation of a Unique Machine Description for Chemical Structures—A Technique Developed at Chemical Abstracts Service. Journal of Chemical Documentation 1965, 5, 107-113.
(49) Ertl, P.; Schuffenhauer, A. Estimation of synthetic accessibility score of drug-like molecules based on molecular complexity and fragment contributions. Journal of cheminformatics 2009, 1, 8.
(50) Landrum, G. RDKit: Open-source cheminformatics. Online). http://www.rdkit.org. Accessed 2006, 3, 2012.
(51) Trott, O.; Olson, A. J. AutoDock Vina: improving the speed and accuracy of docking with a new scoring function, efficient optimization, and multithreading. Journal of computational chemistry 2010, 31, 455-461.
(52) Schwartz, D. M.; Kanno, Y.; Villarino, A.; Ward, M.; Gadina, M.; O'Shea, J. J. JAK inhibition as a therapeutic strategy for immune and inflammatory diseases. Nature Reviews Drug Discovery 2017, 16, 843.
(53) Ivanenkov, T., Balakin New Approaches to the Treatment of Inflammatory Disease. Drugs in R & D 2008, 9, 397-434.
(54) Ivanenkov, Y.; Balakin, K.; Lavrovsky, Y. Small Molecule Inhibitors of NF-kB and JAK/STAT Signal Transduction Pathways as Promising Anti-Inflammatory Therapeutics. Mini reviews in medicinal chemistry 2011, 11, 55-78.
(55) Samadi, A.; Ahmad Nasrollahi, S.; Hashemi, A.; Nassiri Kashani, M.; Firooz, A. Janus kinase (JAK) inhibitors for the treatment of skin and hair disorders: a review of literature. Journal of Dermatological Treatment 2017, 28, 476-483.
(56) Verstovsek, S. Therapeutic potential of JAK2 inhibitors. ASH Education Program Book 2009, 2009, 636-642.
(57) Lancman, G.; Mascarenhas, J. Should we be treating lower risk myelofibrosis patients with a JAK2 inhibitor? Expert review of hematology 2017, 10, 23-28.
(58) Jain, T.; Mesa, R. The development, safety and efficacy of pacritinib for the treatment of myelofibrosis. Expert review of anticancer therapy 2016, 16, 1101-1108.
(59) Gaulton, A. et al. The ChEMBL database in 2017. Nucleic Acids Research 2016, 45, D945-D954.

The invention claimed is:
1. A method for generating an object comprising:
obtaining a plurality of objects and object properties thereof from a dataset, wherein at least an object data is coupled to an object property data;
inputting the plurality of objects and object properties into a machine learning platform;
creating a trained model with the machine learning platform that is trained with the plurality of objects and object properties, wherein the trained model is an entangled conditional adversarial autoencoder that is configured to:
include an encoder that encodes a distribution of latent code to a latent space;
a predictor model configured to extract object property data from latent code and updating the encoder to eliminate extracted object property data from the latent code;
include a discriminator model that forces a distribution on the latent code to match a prior distribution, wherein the discriminator model discriminates between samples of the distribution of the latent code in the latent space and the prior distribution;
include a decoder that decodes the latent code into decoded object data;
consider the object data that is coupled with the object property data; and
concatenating a defined property with the latent code for input into the decoder;
processing the trained model to obtain the distribution of the latent codes of the objects from the encoder;
reparameterizing the latent codes into reparameterized latent codes with the object properties;
disentangling the latent codes from the object properties with a combined disentanglement protocol of a predictive disentanglement with the predictor model and a joint disentanglement with the discriminator model to provide independence between the latent codes and the object properties;
determining a distribution difference loss of distribution of reparameterized latent codes with a defined prior distribution;
determining a property prediction loss of an estimated property prediction;
generating a plurality of generated objects with the decoder from the disentangled latent codes each having the defined property value of the object properties;
determining reconstruction loss of the generated objects from the input plurality of objects;
determining a total loss from the reconstruction loss, distribution difference loss, and property prediction loss, wherein objects with lowest total loss is selected as a candidate object and
providing a report of the plurality of the candidate objects, wherein the report defines at least one defined property value of the plurality of the candidate objects, wherein the objects are molecules and the properties are one or more of physical properties, molecular fingerprint, lipophilicity, synthetic accessibility, biochemical properties, binding activity, or solubility.
2. The method of claim 1, further comprising filtering the dataset to remove objects unlikely to have the defined property value.
3. The method of claim 1, wherein the dataset includes structural data for the plurality of objects and property data for the object properties, wherein the property data includes at least one of: binding activity to a specific protein, solubility, or ease of synthesis of the objects.
4. The method of claim 1, further comprising performing a predictive disentanglement between at least two variables with the trained model.
5. The method of claim 4, further comprising:
estimating dependence between two variables by computing their mutual information; and
promoting independence between the two variables by minimizing their mutual information in computations.
6. The method of claim 5, further comprising:
optimizing loss by training a neural network q to extract information about a first variable of the two variables from the second variable and/or the latent code; and
updating an encoder of the trained model to eliminate the extracted information from the latent code.
7. The method of claim 1, further comprising performing a joint disentanglement between at least two variables with the trained model.
8. The method of claim 7, further comprising:
training the trained model to extract a first property from the latent code; and
modifying a second property to confuse a predictor to obtain a predictive regularizer.

9. The method of claim 8, further comprising:
optimizing the trained model to have conditional independence of a plurality of variables for the plurality of variables;
obtaining a plurality of factorized variational distributions for the plurality of variables; and
optimizing a set of distributions to underestimate any remaining mutual information for the plurality of variables.

10. The method of claim 9, further comprising:
optimizing a factorized prior with independent labels and latent codes;
sampling from a distribution of latent codes with properties of defined objects; and
adversarially training the trained model to bring the sampled distribution closer to the factorized prior to provide disentanglement of the plurality of variables.

11. The method of claim 1, further comprising performing a combined disentanglement between at least two variables with the trained model.

12. The method of claim 11, further comprising:
performing a predictive disentanglement to force independence between at least two marginal distributions of latent codes; and
performing a joint disentanglement to reduce remaining mutual information between the at least two marginal distributions of the latent codes.

13. The method of claim 1, further comprising:
defining the property value of a generated object;
generating structural analogs of a plurality of objects having the property value;
processing the structural analogs through a supervised adversarial autoencoder;
estimating mutual information for the structural analogs; and
reducing the mutual information with a disentanglement procedure.

14. The method of claim 13, further comprising:
sampling lipophilicity data and synthetic accessibility from the dataset;
measuring a correlation coefficient between at least one condition and at least one obtained property of the structural analogs;
removing objects in the dataset from the structural analogs; and
identifying at least one structural analog having the defined property value.

15. The method of claim 14, further comprising:
synthesizing the at last one identified structural analog; and
validating the synthesized at least one structural analog to have the defined property value in vitro or in vivo.

16. The method of claim 14, further comprising providing a report identifying the at least one structural analog having the defined property value and identifying the determined defined property value or a plurality of determined properties thereof.

17. The method of claim 1, comprising at least one of:
the machine learning platform includes two or more trained machine learning models;
machine learning models are neural networks such as fully connected neural networks, convolutional neural networks, or recurrent neural networks;
the trained machine learning model converts the objects into the latent codes;
the trained machine learning model converts the latent codes to the generated objects;
the machine learning platform enforces a certain distribution of latent codes across all potential generated objects;
the two or more trained machine learning models are trained with adversarial training or variational interference;
a separate trained machine learning model is trained to predict object properties from the latent codes; or
a separate trained machine learning model is trained to parameterize a desired distribution of latent codes of objects having the same value of properties.

18. The method of claim 1 comprising at least one of:
an object property is binding affinity for a target protein;
an object property is binding affinity for binding site on the target protein;
an object property is a molecular fingerprint; or an object property is lipophilicity and/or synthetic accessibility.

19. The method of claim 18, wherein:
the target protein is JAK2 and/or JAK3; and/or a binding site is an active site for MCL1.

20. The method of claim 1, further comprising:
synthesizing a physical molecule of at least one of the candidate object molecules; and
validating the synthesized physical molecule to have the defined property value.

21. The method of claim 20, further comprising performing an in vitro experiment with the physical molecule.

22. The method of claim 20, further comprising performing an in vivo experiment with the physical molecule.

* * * * *